(12) United States Patent
Eijkenboom

(10) Patent No.: US 8,673,361 B2
(45) Date of Patent: *Mar. 18, 2014

(54) CYTOKINE MODULATING COMPOSITION

(75) Inventor: Maud Louisa Johanna Maria Eijkenboom, Melville (AU)

(73) Assignee: Cambridge Scientific Pty Ltd, Leederville (AU)

( * ) Notice: Subject to any disclaimer, the term of this patent is extended or adjusted under 35 U.S.C. 154(b) by 870 days.

This patent is subject to a terminal disclaimer.

(21) Appl. No.: 12/226,783

(22) PCT Filed: Apr. 27, 2007

(86) PCT No.: PCT/AU2007/000554
§ 371 (c)(1),
(2), (4) Date: Jul. 7, 2009

(87) PCT Pub. No.: WO2007/124540
PCT Pub. Date: Nov. 8, 2007

(65) Prior Publication Data
US 2009/0305976 A1   Dec. 10, 2009

(30) Foreign Application Priority Data

Apr. 28, 2006 (AU) ................ 2006902205
Aug. 14, 2006 (AU) ................ 2006904367

(51) Int. Cl.
*A61K 35/16* (2006.01)
*A61K 39/00* (2006.01)
*A61K 38/48* (2006.01)

(52) U.S. Cl.
USPC ............. 424/530; 424/184.1; 424/94.64

(58) Field of Classification Search
None
See application file for complete search history.

(56) References Cited

U.S. PATENT DOCUMENTS 2,579,367 A * 12/1951 Stickels et al. ............ 424/447
2006/0182811 A1 * 8/2006 Edwards et al. ........... 424/531

FOREIGN PATENT DOCUMENTS

WO   WO-2006/084334 A1   8/2006

OTHER PUBLICATIONS

Dictionary.com definition of mediate, Dec. 11, 2010: http://dictionary.reference.com/browse/mediate.*
Williams, C.S. et al. Celecoxib prevents tumor growth in vivo without toxicity to normal gut: Lack of correlation between in vitro and in vivo models. Cancer Research, 2000, vol. 60, p. 6045-6051.*
Fleischmann, C.M., et al. Enhanced in vivo sensitivity to interferon with in vitro resistant B16 tumor cells in mice. Cancer Immunology and Immunotherapy, 1994, vol. 39, p. 148-154.*
Landmann, R, et al. Recombinant interferon-g up-regulates in vivo and down-regulates in vitro monocyte CD14 antigen expression in cancer patients. Cancer Immunology and Immunotherapy, 1990, vol. 31, p. 292-296.*
Scopes R.K., "Protein Purification", Principles and Practice 3rd Edn, Springer-Verlag. USA 1994, Chp 4; pp. 71-101.

* cited by examiner

*Primary Examiner* — Robert Landsman
*Assistant Examiner* — Bruce D Hissong
(74) *Attorney, Agent, or Firm* — Edwards Wildman Palmer LLP; Jeffrey D. Hsi

(57) ABSTRACT

The invention relates to an agent having cytokine mediating activity. In particular the invention relates to a composition comprising a fraction of denatured plasma proteins and at least one metal, metal ion or metal salt thereof, wherein said mixture has cytokine mediating activity.

8 Claims, 30 Drawing Sheets

CYTOKINE MODULATING COMPOSITION

CROSS-REFERENCE TO RELATED APPLICATIONS

This application is the National Stage of PCT/AU2007/000554, filed Apr. 27, 2007, which claims benefit of Australian Application 2006902205, filed Apr. 28, 2006 and 2006904367, filed Aug. 14, 2006. The entire contents of each of these applications is incorporated herein by reference.

FIELD

The invention relates to an agent having cytokine mediating activity. In particular the invention relates to a composition having cytokine mediating activity and comprising an effective amount of a fraction separated from plasma admixed with at least one metal, metal ion or metal salt thereof, wherein said mixture has been denatured.

BACKGROUND

Cytokines are soluble proteinaceous substances produced by a wide variety of haemopoietic and non-haemopoietic cell types, and are critical to the functioning of both innate and adaptive immune responses. Apart from their role in the development and functioning of the immune system, and their aberrant modes of secretion in a variety of immunological, inflammatory and infectious diseases, cytokines are also involved in several developmental processes during human embryogenesis. Thus, cytokines often act locally, but can also have effects on the whole body. For example, cytokines are able to interact directly with the evolving biology of an injury, trauma, or disease.

Thus, compounds having cytokine mediating activity have the potential to be used inter alia in the treatment of stroke, AIDS, multiple sclerosis, infection, spinal cord injuries, musculo-skeletal pain, and injuries to the skin. Currently, compounds having cytokine mediating activity have application in rheumatoid arthritis, cancer, stroke, spinal cord injuries, autoimmune diseases, pain, and inflammation.

Currently, there are about 20,000 products sold worldwide for the treatment of pain and inflammation that are based on aspirin or one or its derivatives. As a result these products tend to work in a similar manner and target pain and inflammation in a similar way. All these drugs function by inhibiting prostaglandins, whose roles include the protection of the gastrointestinal lining. In 1998, 16,000 people in the USA alone died from gastrointestinal complications linked to anti-arthritis drugs.

In addition, pain and inflammation involve more than just prostaglandin and thromboxane. In fact, an average painful musculo-skeletal event will involve around 20 cytokines and endotoxins, many of which play a critical role in determining the severity of the body's response to an injury. Three of the most important cytokines in this process are TNF-alpha, IL-1beta, and IL-6.

Therefore there is a continued need for agents having cytokine mediating activity, as these may be useful in the treatment of numerous diseases and disorders, pain, and inflammation.

SUMMARY

Accordingly, in a first aspect, a method of manufacturing a composition having cytokine mediating activity comprising:
  (a) mixing plasma with sodium bicarbonate ($NHCO_3$) and incubating said mixture for sufficient time and at a temperature of no more than 80° to produce a precipitate;
  (b) resolubilising said precipitate in the presence of an aqueous solution at a temperature of between about 80° C. and about 150° C., wherein either before, during or after the resolubilising step at least one metal, metal ion or metal salt thereof is admixed; and
  (c) separating a cytokine mediating fraction from the resolubilised precipitate in step (b), which fraction comprises denatured plasma proteins and at least one metal, metal ion or metal salt thereof.

In some embodiments, a protease eg trypsin is added to steps a or b in order to further enhance denaturation. The protease may be added before or after heating the mixture.

In some embodiments, the step of separating the cytokine mediating fraction is by chromatography such as affinity chromatography, column chromatography, partition chromatography, gel-filtration chromatography with a suitable solvent or solvent mixture.

The fractionation step may be performed by chromatography on a polyamide column; however, any other method of fractionation may be used.

The plasma may be obtained from any animal source. Preferably, the plasma is isolated from an animal selected from the group consisting of human, equine, bovine, ovine, murine, caprine and canine.

The metal, metal ion or metal salt thereof can be any metal. In one embodiment, the metal is selected from the group consisting of nickel, sodium, copper, zinc, cobalt, iron, magnesium, manganese, potassium, silver and mercury, ions or salts thereof and mixtures thereof.

The first heating step (step a) is carried out at no more than 80° C. Preferably, the temperature is between 50° C. and 80° C. More preferably, the temperature is between 60° C. and 70° C. Most preferably, the temperature is about 67° C.

The second heating step (step b) is carried out between about 80° C. and about 150° C. In some embodiments the second heating step is carried out between about 90° C. and about 130° C. In some embodiments the second heating step is carried out at about 120° C. to produce a solubilised precipitate comprising denatured proteins having cytokine mediating activity.

The mixture can be used directly or further separated to produce a fraction having cytokine mediating activity.

In some embodiments, the cytokine mediating activity is selected from the group consisting of TNF-receptor binding, TNF-alpha expression inhibition, TACE inhibition, CCR receptors binding, Caspase inhibition and TNF IL1beta inhibition.

In a second aspect, the present invention provides a composition comprising a fraction of denatured plasma proteins and at least one metal, metal ion or metal salt thereof, wherein said mixture has cytokine mediating activity.

In some embodiments, the composition of the invention comprises at least a fraction of a mixture as described above. In some embodiments, the composition of the invention is admixed with a pharmaceutical carrier. Any pharmaceutical carrier known in the art may be used.

In a third aspect the present invention provides a composition having cytokine mediating activity obtained by:
(a) mixing plasma with sodium bicarbonate (NHCO$_3$) and protease and incubating said mixture for sufficient time and at a temperature of no more than 80° to produce a precipitate;
(b) resolubilising said precipitate in the presence of an aqueous solution at a temperature of between about 80° C. and about 150° C., wherein either before, during or after the resolubilising step at least one metal, metal ion or metal salt thereof is admixed; and
(c) separating a cytokine mediating fraction from the resolubilised precipitate in step (b), which fraction comprises denatured plasma proteins and at least one metal, metal ion or metal salt thereof.

In some embodiments, the step of separating the cytokine mediating fraction is by chromatography such as affinity chromatography, column chromatography, partition chromatography, gel-filtration chromatography with a suitable solvent or solvent mixture.

In a fourth aspect, the present invention provides a method for mediating cytokine levels in a subject, said method comprising administering to the subject an effective amount of a composition comprising a fraction of denatured plasma proteins and at least one metal, metal ion or metal salt thereof.

The method of administration may be any method known in the art. The composition may be administered topically, systemically, intramuscularly, subcutaneously, intraperitoneally, intrapleurally, intraarticularly, intrathecally, rectally, vaginally, or by inhalation. In some embodiments the composition is administered topically.

In a fifth aspect, the invention provides a composition for mediating cytokine levels in a subject, comprising a pharmaceutically acceptable carrier and an effective amount of a composition comprising a fraction of denatured plasma proteins and at least one metal, metal ion or metal salt thereof.

In a sixth aspect, the invention provides a physiologically active substance which is extracted from a mixture of plasma and at least one metal, metal ion or metal salt thereof, wherein said mixture has been denatured.

In some embodiments the physiologically active substance is further admixed with a pharmaceutically acceptable carrier. Preferably, the carrier is at least one member selected from the group consisting of distilled water, physiologically saline solution, Ringer's solution, plant oil, synthetic fatty acid glycerides, higher fatty acid esters, propylene glycol, lactose, mannitol, corn starch, crystalline cellulose, gum arabicum, gelatin, potato starch, carmerose, carmerose calcium, talc, and magnesium stearate.

In a seventh aspect, the invention provides a method for treating a disease or disorder, comprising administering a fraction having cytokine mediating activity and separated from a mixture of plasma and at least one metal, metal ion or salt thereof, wherein said mixture has been denatured and wherein said fraction is admixed with a pharmaceutically acceptable carrier. The disease or disorder may be associated with pain and/or inflammation.

In an eighth aspect, the invention provides use of a composition made by the method of the first aspect in the manufacture of an agent used to treat a disease or disorder associated with aberrant cytokine activity.

In a ninth aspect, the present invention provides an analgesic and anti-inflammatory composition comprising an effective amount of soluble plasma proteins consisting essentially of protein or protein fragments having molecular weights less than 50 kDa as determined by SDS-PAGE.

In a tenth aspect the present invention provides an analgesic and anti-inflammatory composition obtained by:
(a) providing plasma;
(b) exposing said plasma to sodium bicarbonate (NaHCO$_3$); and
(c) exposing the plasma from step (b) to a protease solution for sufficient time to produce a soluble plasma protein composition comprising protein or protein fragments with molecular weights of less than 50 kDa, which composition has analgesic and anti-inflammatory activity.

BRIEF DESCRIPTION OF THE FIGURES

FIG. 1 (right panel) shows a 12% SDS-PAGE Tricine gel. Proteins were silver-stained Lane 5 contains molecular weight markers. Lane 6 shows untreated bovine plasma. This gel shows that the majority of proteins in unpurified bovine plasma are in a size range of 50-80 kilodaltons.

DETAILED DESCRIPTION OF PREFERRED EMBODIMENTS

Figure 1:
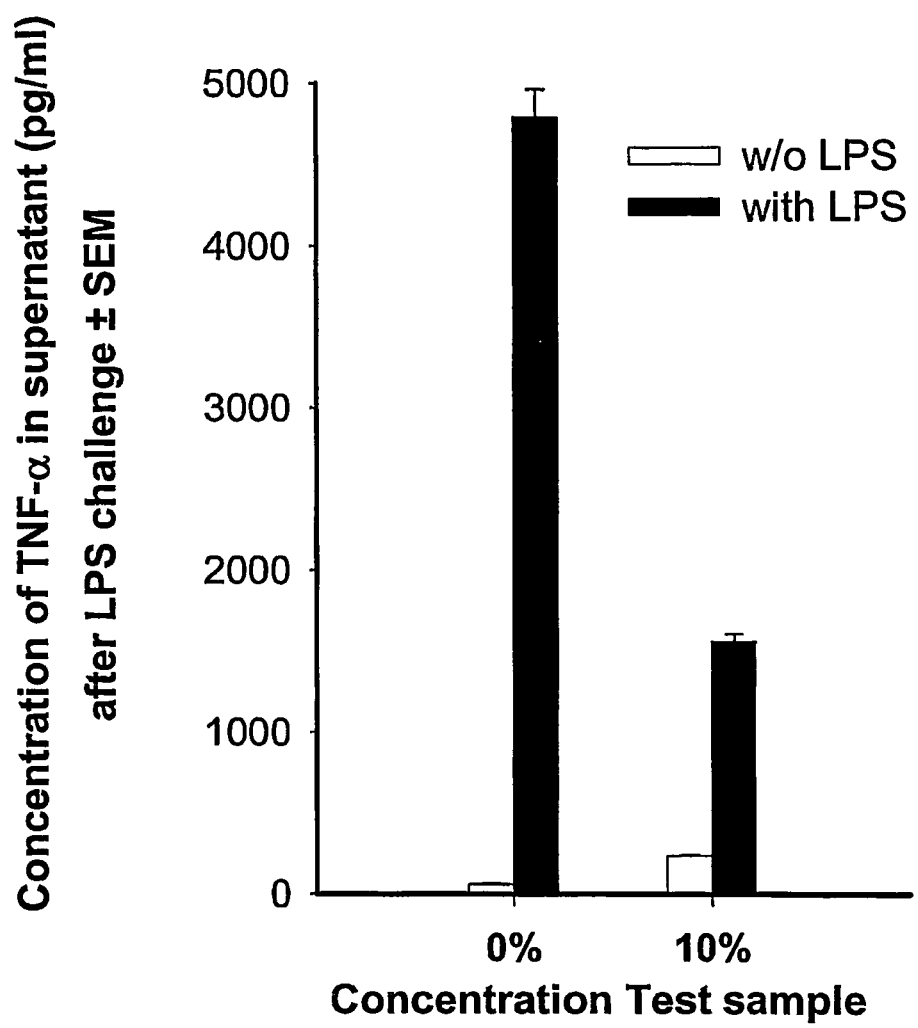
FIG. 1 shows the effect of one form of the composition of the present invention (TEST SAMPLE) comprising zinc chloride, glycine and trypsinised protein on the TNF-α production by LPS-stimulated human monocytes.

Before describing the invention in detail, it is to be understood that it is not limited to particularly exemplified methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional chemistry and pharmacology within the skill of the art. Such techniques are well known to the skilled worker, and are explained fully in the literature. See, eg., Coligan, Dunn, Ploegh, Speicher and Wingfield "Current protocols in Protein Science" (1999) Volume I and II (John Wiley & Sons Inc.); The Merck Index, 12th Edition (1996), Therapeutic Category and Biological Activity Index; and Remington's Pharmaceutical Sciences, 17$^{th}$ Edition, Mack Publishing Company, Easton, Pa., USA.

It must be noted that as used herein and in the appended claims, the singular forms "a," "an," and "the" include plural reference unless the context clearly dictates otherwise. Thus, for example, a reference to "a metal" includes a plurality of such metals, and a reference to "an isolated protein" is a reference to one or more proteins, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In its broadest aspect, the invention provides a composition having cytokine mediating activity. As used herein, the term "cytokine mediating activity" means the, for example composition, reduces, inhibits, or elevates the activity of a cytokine. For example, cytokines are known to be associated with pain and inflammation. Therefore a composition having cytokine mediating activity may reduce or inhibit pain and/or inflammation caused by a cytokine. For example, some cytokines and combinations of cytokines may exert a beneficial effect on a subject, cell, or tissue, such as mediating apoptosis. Therefore a composition having cytokine mediating activity may increase or up-regulate such cytokines.

In some embodiments, the cytokine mediating activity is selected from the group consisting of TNF-receptor binding, TNF-alpha expression inhibition, TACE inhibition, CCR receptors binding, Caspase inhibition and TNF IL1beta inhibition.

In some embodiments, the composition having cytokine mediating activity has anti-inflammatory activity and/or analgesic activity. It will be appreciated that the term "anti-inflammatory" is intended to include an inflammatory response modifier, including all inflammatory responses such as production of stress proteins, white blood cell infiltration, fever, pain, swelling and so forth. Furthermore, the terms "analgesic," "analgesia," and "analgesically" as used herein interchangeably are intended to include a pain reliever that is capable of reducing pain sensation or nociception, whether the pain incurred is a result of disease, inflammation, trauma or psychosomatic reaction.

The compositions of the present invention can therefore be administered as an effective amount to a subject in need of analgesia or anti-inflammatory treatment. The phrase "in need of analgesia" as applied to a subject herein embraces a subject suffering mild to intense pain at the time of administration of the composition of the present invention, as well as a subject that can reasonably be expected to have an imminent onset of mild to intense pain, eg., within about 1 to about 2 hours and especially within about 30 minutes, if no analgesic is administered.

An "effective pain-relieving concentration" or "effective pain-relieving plasma concentration" as used herein is intended to mean a plasma level in a subject which when tested in a standardized test involving subject scoring of the severity of pain, achieves a mean score indicating pain relief. In one such test as described herein below, patients score pain on a scale of from 0 (no reduction in severity of pain) to 4 (complete relief of pain) and a mean score equal to or greater than a given value is deemed to constitute effective pain-relief. A mean score of 0.5 or greater and, more preferably, 1.0 or greater in such a test, as exemplified herein, is deemed to constitute effective pain relief. The skilled artisan will appreciate, however, that other approaches can be used to assess the severity of pain and relief from such pain.

Thus, one aspect of the present invention involves a therapeutic method for analgesia in which a composition comprising the composition of the present invention is administered to a subject, in a formulation which provides detectable pain relief. By "detectable pain relief", it is meant that the formulation produces effective pain relief which is measurable by a standard method such as described above. For example, a formulation, which achieves a mean score of 0.5 or greater and, more preferably, 1.0 or greater on a scale of from 0 to 4 in a testing system as described above, is deemed to provide detectable pain relief. The invention is not limited to use of any particular type of formulation, so long as it exhibits the pharmacokinetic profile defined herein. Examples of suitable formulation types are described below.

In some embodiments, the compositions of the present invention essentially comprises a mixture of plasma proteins and at least one metal, metal ion or metal salt, wherein the plasma proteins have been denatured.

In other embodiments, the compositions of the present invention consist essentially of protein or protein fragments isolated from plasma, wherein the protein or protein fragments have molecular weights less than 50 kDa as determined by SDS-PAGE.

In some embodiments of the invention involves a method in which a composition of the invention is administered to a subject to provide reduced cytokine activity. The composition may be in a form of a formulation. The invention is not limited to use of any particular type of formulation, so long as it exhibits the pharmacokinetic profile defined herein. Examples of suitable formulation types are described below.

The term "plasma" are used herein typically refers to the straw-coloured fluid in which the blood cells are suspended. It consists of various inorganic salts of sodium, potassium, calcium etc. with a high concentration of protein (approximately 70 g/l) and a variety of trace elements.

The plasma used in the present invention may be obtained from any animal source as plasma can be prepared from the blood of any animal. In some embodiments, the plasma is isolated from blood taken from an animal selected from the group consisting of human, equine, bovine, ovine, murine, caprine and canine. In some embodiments, the animal source for the plasma is bovine.

Plasma can be obtained by any method know in the art. For example, techniques shown in U.S. Pat. No. 5,872,227 entitled "Process for separation of components from red blood cells"; U.S. Pat. No. 5,252,221 entitled "Method for purifying blood plasma"; U.S. Pat. No. 5,145,706 entitled "Method for preparation of plasma powder and product thereof"; U.S. Pat. No. 5,011,695 entitled "Sterilization of blood and its derivatives with vitamins"; U.S. Pat. No. 4,746,730 entitled "Bio-available iron-protein derivatives and process for their preparation" may all be used to produce plasma useful in the present invention. All of these patents are incorporated in their entirety herein by reference.

In some embodiments, the plasma is obtained using the methods disclosed in U.S. Pat. No. 4,610,814 entitled "Process for the preparation of protein concentrates and nutriments by processing animal blood" to Dede et al. In other embodiments, the plasma is produced by the methods disclosed in the Applicants co-pending International Patent Application No. PCT/AU2006/000185. This patent and application are incorporated in their entirety herein by reference.

The plasma may be freshly isolated or lyophilised. In some embodiments, blood is isolated from cattle and the haemoglobin is removed by standard procedures.

The plasma is then admixed or exposed to about 1 to about 4% w/w sodium bicarbonate. The term "about" means that the amount of sodium bicarbonate used in treating the plasma will have a final concentration of 1% give or take around 10% e.g. 0.9% or 1.1%. The "exposing" as used herein refers to the time the plasma and sodium bicarbonate are mixed together or in contact with each other. In some embodiments, the plasma is exposed to the sodium bicarbonate for 4-5 hours.

The plasma/sodium bicarbonate mixture is incubated at a temperature, wherein the temperature is gradually raised from room temperature to 70-80° C. after the 1% sodium bicarbonate has been added to the plasma. After this step a precipitate forms.

In some embodiments, a protease selected from the group consisting of trypsin, chymotrypsin, factor Xa, venom-protease, thrombin, plasmin and a serine-protease of the subtilisin family is added before heating or after heating to about 80° C. In some embodiments the protease is trypsin.

The precipitate is then resolubilised by mixing the precipitate or the lyophilised precipitate with water or other aqueous solutions (approximately 50 g per liter) and heating the mixture (second heating step) at between about 80° C. and about 150° C. In some embodiments the second heating step is carried out between about 90° C. and about 130° C. In some embodiments the second heating step is carried out at about 120° C.

At this stage i.e. before, after or during the resolubilisation step at least one metal, metal ion or salt thereof is added to the resolubilised plasma proteins. Various metals and/or metal ions are useful in the composition of the present invention and as such the present invention embraces all such metals or metal ions.

In some embodiments, the metals are selected from the group consisting of nickel, sodium, copper, zinc, cobalt, iron, magnesium, manganese, potassium, silver and mercury.

In cases where the metals are sufficiently basic or acidic to form stable non-toxic acid or base salts, the use of the metals as salts can be appropriate. Examples of acceptable metal salts include acetate, ascorbate, benzoate, bicarbonate, chloride, citrate, carbonate, α-glycerophosphate, α-ketoglutarate, malonate, methanesulfonate, nitrate, succinate, sulfate, tartarate and tosylate salts.

Metal salts can be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts can be made.

For example, the metal may be silver (I), wherein the nitrate salt provides adequate free silver (I) ion to provide the necessary metal requirement. The chloride salt on the other hand provides less silver, being less soluble and with a low dissociation constant and therefore is less useful in the invention. The skilled artisan will be able to readily determine the suitable salt form of the metal ion that provides the necessary properties for the present invention. Furthermore, the skilled artisan will be aware of the compatibility of the salt forms of the metal(s) and other components of the composition to maintain adequate levels of the metal ion(s).

In some embodiments, the metals used in the composition comprise a mixture of a number of metals. For example, the mixture of metals could consist essentially of $NiSO_4.7H_2O$, $NH_4VO_3$, $NaF$, $CuSO_4.5H_2O$, $ZnCl_2$, $(NH_4)_6MO_7O_{24}.4H_2O$, $COCl_2.6H_2O$, $FeSO_4.7H_2O$, $MgSO_4.7H_2O$, $H_3BO_3$, $MnCl_2.4H_2O$ and $K_2CrO_4$.

Once the resolubilised plasma protein mixture comprising denatured plasma proteins and metal, metal ion or salts thereof has been obtained it can be either used directly or fractionated to obtain a more refined fraction having cytokine mediating activity. Techniques for fractionating protein-containing mixtures are well known in the art. See, for example, "Plasma Protein Fractionation" Heide K, Haupt H & Schwick H; in The Plasma Proteins, 2nd Edition Vol 3 (1977) Putnam F. (Ed); U.S. Pat. No. 4,351,710 and U.S. Pat. No. 4,322,275 both entitled "Fractionation of protein mixtures"; U.S. Pat. No. 5,138,034 entitled "Method of fractionating plasma proteins" all incorporated herein by reference.

As described above, in some embodiments, the invention provides a method of reducing or elevating cytokine activity in a subject, the method comprising administering to the subject an effective amount of a composition of the invention.

The composition of the invention is useful for treatment of non-human mammalian subjects, including domestic, farm and exotic animals, such as for example dogs horses, zoo animals and the like, but is primarily useful for the treatment of humans.

Generally, the terms "treating," "treatment" and the like are used herein to mean affecting a subject, or its tissue or cells, to obtain a desired pharmacological and/or physiological effect. The effect may be prophylactic in terms of completely or partially preventing cytokine mediated disease or sign or symptom thereof, and/or may be therapeutic in terms of a partial or complete cure of the cytokine mediated disease. "Treating" as used herein covers any treatment of, or prevention of cytokine mediated disease in a vertebrate, a mammal, particularly a human, and includes: (a) preventing the cytokine mediated disease from occurring in a subject that may be predisposed to the cytokine mediated disease, but has not yet occurred; (b) inhibiting the cytokine mediated disease, i.e., arresting its development; or (c) relieving or ameliorating the symptoms of the cytokine mediated disease, i.e., cause regression of the symptoms of the cytokine mediated disease.

Compositions of the invention can also be used in combination therapies with opioids and other analgesics, including narcotic analgesics, Mu receptor antagonists, Kappa receptor antagonists, non-narcotic (i.e., non-addictive) analgesics, monoamine uptake inhibitors, adenosine regulating agents, cannabinoid derivatives, Substance P antagonists, neurokinin-1 receptor antagonists and sodium channel blockers, among others. Preferred combination therapies comprise a composition useful in methods of the invention with one or more compounds selected from aceclofenac, acemetacin, α-acetamidocaproic acid, acetaminophen, acetaminosalol, acetanilide, acetylsalicylic acid (aspirin), S-adenosylmethionine, alclofenac, alfentanil, allylprodine, alminoprofen, aloxiprin, alphaprodine, aluminum bis(acetylsalicylate), amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antipyrine salicylate, antrafenine, apazone, bendazac, benorylate, benoxaprofen, benzpiperylon, benzydamine, benzylmorphine, bermoprofen, bezitramide, α-bisabolol, bromfenac, p-bromoacetanilide, 5-bromosalicylic acid acetate, bromosaligenin, bucetin, bucloxic acid, bucolome, bufexamac, bumadizon, buprenorphine, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamide, crotethamide, desomorphine, dexoxadrol, dextromoramide, dezocine, diampromide, diclofenac sodium, difenamizole, difenpiramide, diflunisal, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic acid, glafenine, glucametacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lomoxicam, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paranyline, parsalmide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phenyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetradrine, thiazolinobutazone, tiaprofenic acid, tiaramide, tilidine, tinoridine, tolfenamic acid, tolmetin, tramadol, tropesin, viminol, xenbucin, ximoprofen, zaltoprofen and zomepirac (see The Merck Index, 12th Edition (1996), Therapeutic Category and Biological Activity Index, lists therein).

Still other suitable formulations for use in the present invention can be found in Remington's Pharmaceutical Sciences, Mace Publishing Company, Philadelphia, Pa. 17th ed. (1985).

The terms "administration," administering," and "administered" are used herein interchangeably. The anti-cytokine composition of the present invention may be administered orally including sublingual, topically, or parenterally in dosage unit formulations containing conventional non-toxic pharmaceutically acceptable carriers, adjuvants, and vehicles. The term "parenteral" as used herein includes subcutaneous injections, aerosol, intravenous, intramuscular, intrathecal, intracranial, injection or infusion techniques or rectal or vaginally. In some embodiments the composition of the invention is administered together with a pharmaceutically acceptable carrier or diluent compatible with the composition. In preparing such a composition, any conventional pharmaceutically acceptable carrier can be utilised.

The carrier material can be an organic or inorganic inert carrier material suitable for administration to a subject. Suitable carriers include water, gelatin, gum arabic, lactose, starch, magnesium stearate, talc, vegetable oils, polyalkylene-glycols, petroleum jelly and the like. Furthermore, the pharmaceutically active preparations may contain other pharmaceutically active agents. Additionally, additives such as flavouring agents, preservatives, stabilisers, emulsifying agents, buffers and the like may be added in accordance with accepted practices of pharmaceutical compounding.

When a composition of the invention is administered orally, it is generally administered at regular intervals, conveniently at meal times or once daily. A composition of the invention can be made up in any conventional form including: (a) solid form for oral, rectal or vaginal administration such as tablets, capsules (eg. hard or soft gelatine capsules), pills, sachets, powders, granules, and the like; and (b) preparations for topical administrations such as solutions, suspensions, ointments, creams, gels, micronised powders, sprays, aerosols and the like; (c) liquid formulations for intravenous administrated may also be prepared. Pharmaceutical preparations may be sterilised and/or may contain preservatives, stabilisers, wetting agents, emulsifiers, salts for varying the osmotic pressure and/or buffers.

For topical administration to the skin or mucous membrane a composition of the invention may be prepared as an ointment, tincture, cream, gel, solution, lotion, spray; aerosol and dry powder for inhalation, suspension and the like. In fact, any conventional methods of preparing topical compositions can be utilised in this invention. The composition of the invention may be applied in the form of an ointment, gel, cream, lotion, spray; aerosol or dry powder for inhalation. A pharmaceutical preparation for topical administration to the skin can be prepared by mixing the anti-cytokine composition of the present invention with non-toxic, therapeutically inert, solid or liquid carriers customarily used in such preparation. These preparations generally contain 0.01 to 5.0 percent by weight, preferably 0.1 to 1.0 percent by weight, of a composition of the invention, based on the total weight of the peptide preparation.

In preparing the topical preparations described above, additives such as preservatives, thickeners, perfumes and the like conventional in the art of pharmaceutical compounding of topical preparation can be used. In addition, conventional antioxidants or mixtures of conventional antioxidants can be incorporated into the topical preparations containing the afore-mentioned active agent. Among the conventional antioxidants which can be utilised in these preparations are included N-methyl-a-tocopherolamine, tocopherols, butylated hydroxyanisole, butylated hydroxytoluene, ethoxyquin and the like. Cream-base pharmaceutical formulations containing the anti-cytokine composition, used in accordance with this invention, are composed of aqueous emulsions containing a fatty acid alcohol, semi-solid petroleum hydrocarbon, ethylene glycol and an emulsifying agent.

Ointment formulations containing a composition of the invention may comprise admixtures of a semi-solid petroleum hydrocarbon with a solvent dispersion of the anti-cytokine composition. Cream compositions a composition of the invention may comprise emulsions formed from a water phase of a humectant, a viscosity stabiliser and water, an oil phase of a fatty acid alcohol, a semi-solid petroleum hydrocarbon and an emulsifying agent and a phase containing anti-cytokine composition dispersed in an aqueous stabiliser-buffer solution. Stabilisers may be added to the topical preparation. Any conventional stabiliser can be utilised in accordance with this invention. In the oil phase, fatty acid alcohol components function as a stabiliser. These fatty acid alcohol components function as a stabiliser. These fatty acid alcohol components are derived from the reduction of a long-chain saturated fatty acid containing at least 14 carbon atoms.

Formulations for aerosols are described in Drugs and Pharmaceutical Sciences, Marcel Dekker, New York, 72: 547-574 (1996). Furthermore, the anti-cytokine composition of the present invention can be delivered by dry powder inhalation. Such formulations and devices are described in Pharmaceutical Technology, June 1997, pp. 117-125.

Depending upon the mode or type of administration and the level of reduction or elevation of cytokine activity required, the treatment regime will vary. However, typically an individual is monitored hourly or daily, depending on the above factors, and the status of anti-cytokine activity is determined. Administration of a composition of the invention will typically continue until the required level of cytokine activity in the subject is obtained.

Protocols for conducting human pharmacokinetic studies are well known in the art and any standard protocol can be used to determine whether a particular composition of the invention satisfies the pharmacokinetic criteria set out herein. An example of a suitable protocol is described below.

In some embodiments, the compositions of the invention, upon administration, reduce the amount of TNF-α and/or IL-1beta present in an individual's tissue as compared to untreated tissue. Accordingly, the invention encompasses a method of reducing the amount of TNF-α and/or IL-1beta in an individual's tissue comprising the step of administering an effective amount of a composition comprising an effective amount of a fraction separated from plasma and at least one metal, metal ion or metal salt thereof, wherein said mixture has been denatured, wherein the composition reduces the amount of TNF-α in the individual's tissue compared to untreated tissue.

The term "effective amount" refers to that amount which is sufficient to reduce, inhibit, or elevate cytokine activity in a subject. Equally, the term "effective amount" when used with reference to a composition's cytokine mediating activity means the amount sufficient to reduce, inhibit, or elevate the cytokine activity in a subject. What constitutes an effective amount, or dose, of a composition of the invention depends, among other factors, on the body weight of the subject and the reduction or elevation in cytokine activity required. Normally an effective dose will be found in the range of about 1 to about 6 mg/kg body weight. For an average 75 kg subject, this range equates to a dose of about 75 to about 450 mg. Proportionately smaller or larger doses can be appropriate for subjects having lesser or greater body weight. Such a dose can be administered as needed, but typically administration 1 to about 4 times per day, in most cases 1 or 2 times a day, provides an adequate reduction or elevation in cytokine activity.

By "comprising" is meant including, but not limited to, whatever follows the word comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The invention will now be further described by way of reference only to the following non-limiting examples. It should be understood, however, that the examples following are illustrative only, and should not be taken in any way as a restriction on the generality of the invention described above. In particular, while the invention is described in detail in relation to the use of specific animal plasma and metals, it will be clearly understood that the findings herein are not limited to these ingredients.

Example 1

Preparation of Cytokine Mediating Composition 200 liters of sterile cattle blood was centrifuged at 1000-1300×g for 10 minutes and the haemoglobin was removed from the plasma. After centrifugation approximately 100 liters of plasma was gained, and transferred into a dish, suitable for heating and continuous mixing. To the plasma liquid 2 kg Sodium Bicarbonate ($NaHCO_3$) was added and mixed until the $NaHCO_3$ dissolved, then the solution was heated to 80° C. Denatured plasma protein was then recovered and placed on filter paper to dry. The solid sediment was then pressed to produce a 60 kg solid plasma-protein "block" which was then lyophilised by standard procedures. After this process the plasma-protein weighed approximately 8 kg and was used in the preparation of the anti-cytokine preparation as described below.

A solution was then prepared comprising 152 liters of water, 8 kg dried plasma-protein as prepared above and 200 ml of a metal-containing solution. The constituents of the metal-containing solution are shown in Table 1.

TABLE 1

| METAL-CONTAINING SOLUTION | |
|---|---|
| Ni $SO_4$ 7 $h_2O$ | 10.4 g/l |
| $NH_4VO_3$ | 1.2 g/l |
| Na F | 24.0 g/l |
| Cu $SO_4$ 5$H_2O$ | 20.0 g/l |
| ZN $Cl_2$ | 47.0 g/l |
| $(NH_4)6$ $MO_7O_{24}$ 4$H_2O$ | 7.0 g/l |
| CO $Cl_2$ 6$H_2O$ | 20.0 g/l |
| Fe $SO_4$ 7$H_2O$ | 100.0 g/l |
| $MgSO_4$ 7$H_2O$ | 80.0 g/l |
| $H_3BO_3$ | 23.0 g/l |
| Glucose | 50.0 g/l |
| Mn $Cl_2$ 4$H_2O$ | 36.4 g/l |
| $K_2CrO_4$ | 1.0 g/l |
| Glycine | 75.0 g/l |
| Citric Acid | 20.0 g/l |

Made up in a 200 ml solution with water, which was then stirred for at least 20 minutes.

The mixture was then heated up to 120° C. and maintained for two hours with constant mixing. During this time the plasma-protein dissolved and was sterilized. The resulting material was then held at a temperature of about 35° C. and 0.125 g/l of trypsin was added. The material was then allowed to incubate for approximately 2 hours. The digested material was then autoclaved and cooled to produce the anti-cytokine composition of the present invention.

Example 2

Manufacture of Topical Cytokine Mediating Composition

A composition comprising the ingredients shown in Table 2 were mixed at 75-80° C. in a 250 liter vacuum homogenizer equipped with anchor and turbo mixers. Then the ingredients shown in Table 3 were added and the mixing was continued at 80-83° C. for 10 minutes with the aid of the turbo mixer.

A slow cooling process was then carried out using the anchor mixer. When the material reached 60° C., the vacuum was switched on until the end of the cooling.

At 40-45° C. the ingredients shown in Table 4 were added and mixed for 10 minutes. Mixing with the anchor mixer was continued until the mixture reached 25° C.

After a standing period of approximately 24 hours, the anti-cytokine mixture was ready for use.

TABLE 2

| Item No. | Amount Per Kg | Ingredients |
| --- | --- | --- |
| 1 | 20 g | Liposorb S20 (Tween 60) |
| 2 | 20 g | Cremaphor A6 |
| 3 | 10 g | Hydromyristenol |
| 4 | 40 g | Cetyl alcohol |
| 5 | 70 g | Corn Oil (Cold Pressed) |
| 6 | 30 g | Wheat Germ Oil |
| 7 | 0.24 g | Carrot Oil |
| 8 | 50 g | Isopropyl Myristate |
| 9 | 0.2 g | Butylated Hydroxytoluene B.P. |
| 10 | 3 g | Phenonip |

TABLE 3

| 11 | 400 g | Plasma protein from Example 1 |
| --- | --- | --- |
| 12 | 15 g | Propylene Glycol B.P. |
| 13 | 15 g | Hygroplex HHG |
| 14 | 2 g | Allantoin |
| 15 | 208 g | Purified Water B.P. |
| 16 | 10 g | Germaben II |
| 17 | 4 g | Veegum |
| 18 | 100 g | Purified Water B.P. |
| 19 | 0.04 ml | Potassium Bromide 50 g/l |
| 20 | 30.7 mg | Sodium Sulphide |
| 21 | 0.04 ml | Potassium Iodide 25 g/l |

TABLE 4

| 22 | 1.4 g | Chamomile Fragrance |
| --- | --- | --- |

Methodology
1). Add items 1 to 10 in a 250 liter steam pan and heat 75° C.;
2). Boil items 15 and 18 in the 150 liter pan and transfer 13 liters to the 50 liter pan and add Veegum and mix until homogeneous;
3). Add item 14 to the remainder of the Purified Water B. P. in the 150 liter steam pan at above 90° C. and mix. When dissolved add the items 12, 13 and 16 and maintain temperature at 75° C. with continual mixing;
4). Add the water phase (step 5) to the oil phase (step 3) and mix using a short shaft air mixer. Then add step 4 to this using a plastic sieve to ensure that no lumps are incorporated;
5). Add plasma protein from Example 1 and emulsify for 20 minutes, then continue stirring whilst water cooling to 40° C.;
6). Add items 19 to 21 allowing a few minutes in between each addition whilst mixing. Cool to below 30° C.

Example 3

Test of Composition on TNF-α, IL-1Beta, and IL-6 Production by LPS-Stimulated Human Monocytes TNF-α, IL-1beta, and IL-6 are cytokines known to be released as a result of early inflammatory responses, and during healing processes. In the present experiment the aim was to demonstrate that the compositions of the invention were capable of regulating or affecting the presence of TNF-α, IL-1beta, and/or IL-6. It was hypothesised that if the TNF-α, IL-1beta, and/or IL-6 levels were modulated in the assay then this demonstrated that the compositions of the invention had cytokine mediating activity.

Monocytes were isolated from buffy coats by counter current elutriation centrifugation (Brahmi et al., 1983, Ann Immunol (Paris) 134D(2): 191-206) from human blood. Essentially, buffy coats were diluted in RPMI 1640 medium (Life Technologies), and peripheral blood mononuclear cells (PBMC) were isolated by density gradient centrifugation with Ficoll-Hypaque (Amersham Pharmacia Biotech). Monocytes were isolated from the PBMC by counter-current elutriation centrifugation as described above. Monocyte purity was determined by CD14 immunophenotyping. Monocytes isolated by this method were typically 80-90% pure. Monocytes were resuspended at a concentration of $1 \times 10^6$ cells/ml RPMI 1640 medium (Rowell Park Memorial Institute, Sigma-Aldrich) containing 2 mM glutamine, 50 μM 2-mercaptoethanol, 5 μg/ml gentamicin, 2 mM MOPS buffer (Sigma-Aldrich) and 1% foetal calf serum (FCS). Monocytes were cultured under humidified conditions in 48 well culture plates (0.5 ml/well) at 37° C. in 5% $CO_2$.

Next day monocytes were counted and $5 \times 10^5$ cells per well aliquots placed into wells of a 96 well tissue culture plate. The volume was made up to 500 μL per well and then the cells were stimulated with 500 ng/mL lipopolysaccharide (LPS) in the presence of 1% Fetal Calf Serum (FCS), with varying concentrations of test composition for 24 hours. In the present experiment, the test composition was that described in Example 1, except that the metal-containing solution was a simplified version of the metal-containing solution described in Table 1 in that it only contained zinc chloride and glycine.

TNF-α, IL-1beta, and IL-6 levels in the culture supernatants were measured by ELISA Opti EIA, BD Bioscience following the manufacturer's instructions.

The concentrations of test composition used were 10% (50 μL); and 0%. The control was LPS (500 ng/mL) and there were 3 repeats.

Figure 2:
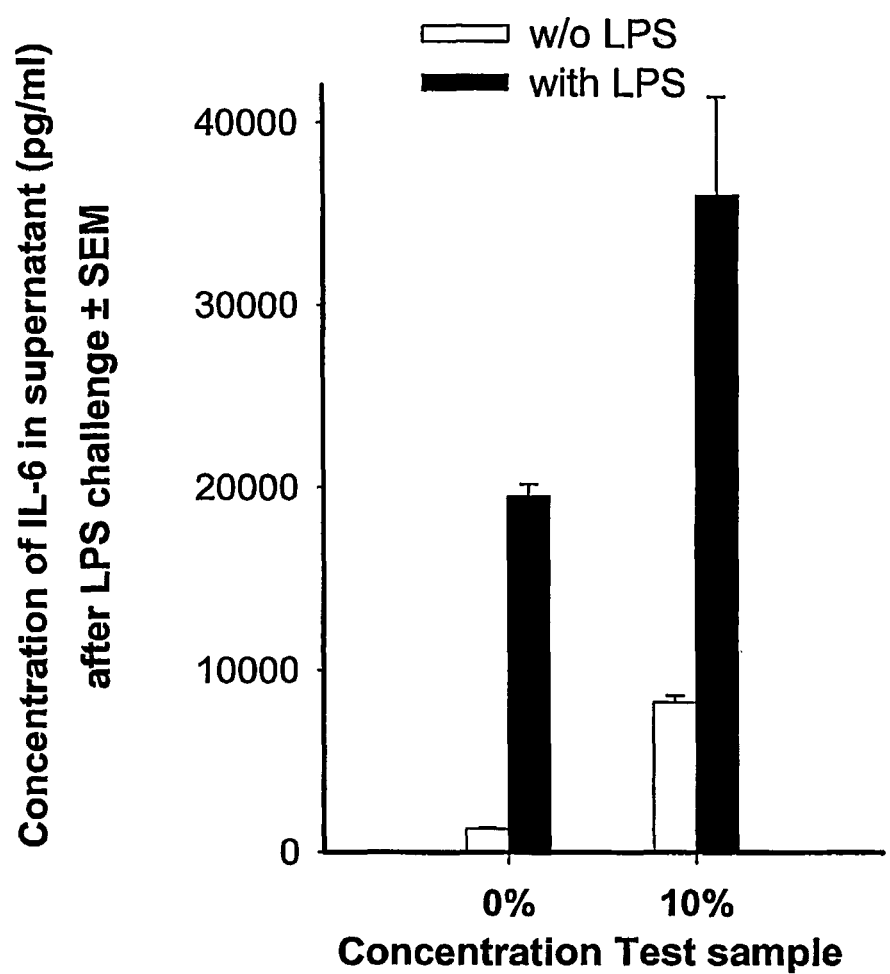
FIG. 2 shows the effect of one form of the composition of the present invention (TEST SAMPLE).
Figure 3:
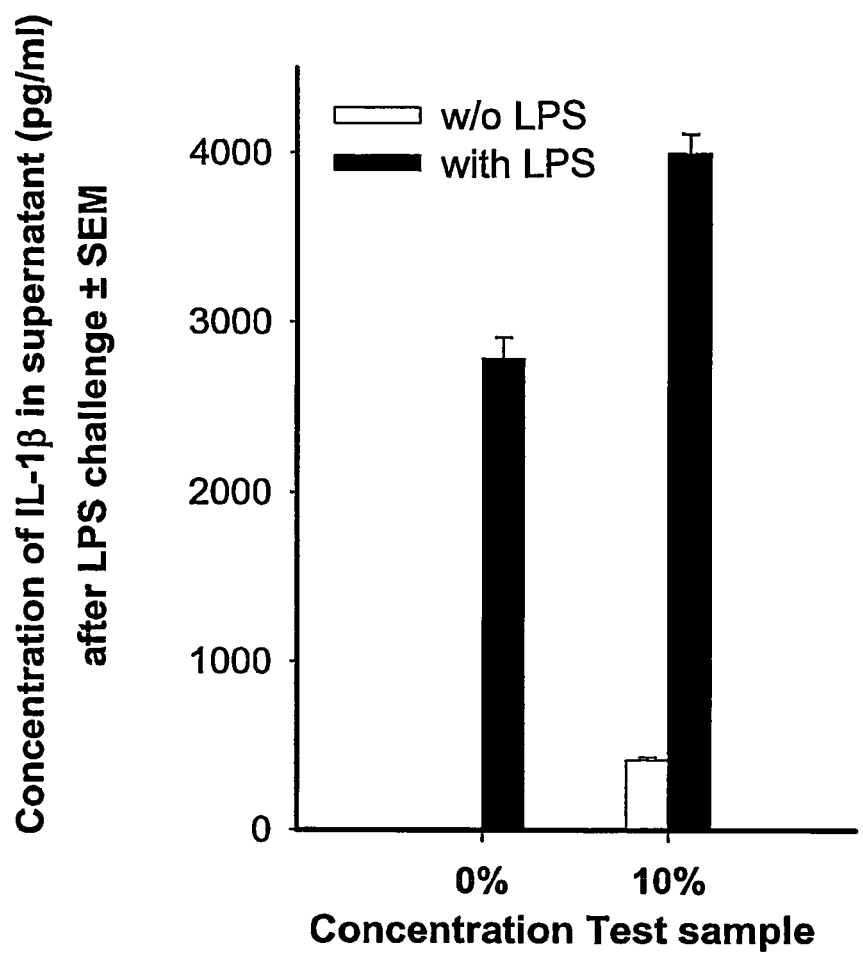
FIG. 3 shows the effect of one form of the composition of the present invention (TEST SAMPLE).

Tables 5, 6, and 6 together with FIGS. 1, 2, and 3 show the results.

TABLE 5

| TNFalpha | | | | | |
| --- | --- | --- | --- | --- | --- |
| Av pg/mL | Control | LPS | SEM | Control | LPS |
| Test sample old 10% | 238.91 | 1562.79 | Test sample old 10% | 4.48 | 45.11 |
| Control | 58.74 | 4792.40 | Control | 4.77 | 165.95 |

TABLE 6

| | IL-1beta | | | | |
|---|---|---|---|---|---|
| Av pg/mL | Control | LPS | SEM | Control | LPS |
| TEST SAMPLE old 10% | 417.90 | 3997.94 | TEST SAMPLE old 10% | 14.88 | 114.92 |
| Control | −55.84 | 2786.00 | Control | 11.43 | 122.65 |

TABLE 7

| | IL-6 | | | | |
|---|---|---|---|---|---|
| Av pg/mL | Ctrl | LPS | SEM | Ctrl | LPS |
| TEST SAMPLE 10% exp 7 | 8245.25 | 36005.93 | TEST SAMPLE 10% exp 7 | 362.57 | 5390.93 |
| Control exp 7 | 1286.22 | 19518.78 | Control exp 7 | 71.41 | 651.99 |

SEM: Standard Error of the Mean

The conclusions that can be drawn from the results are that the test sample decreases LPS-induced TNF-alpha secretion, but increase LPS-induced IL-1beta, and IL-6 secretion in human monocytes, indicating cytokine modulating activity of the test sample.

Example 4

Second Test of Composition on TNF-α Production by LPS-Stimulated Human Monocytes This experiment was essentially a repeat of the experiment described in Example 3 with respect to TNFalpha, with the only difference being the metal-containing solution. In the present experiment, the test composition was that described in Example 1, except that the metal-containing solution contained only copper sulphate.

Figure 4:
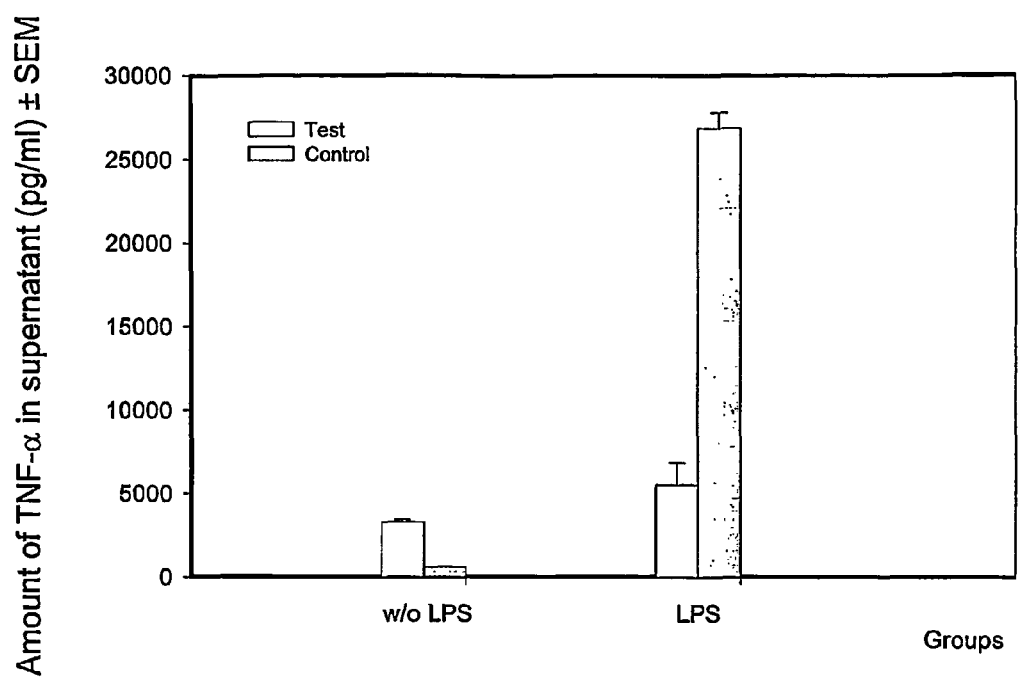
FIG. 4 shows the effect of the composition of the present invention, containing copper as the metal-containing solution, on the TNF-α production by LPS-stimulated human monocytes.

Table 8 and FIG. 4 show the results.

The conclusions that can be drawn from these results are that the test sample decreases TNF-alpha levels of human monocytes to an LPS challenge.

TABLE 8

| Av pg/mL | Ctrl | LPS | SEM | Ctrl | LPS |
|---|---|---|---|---|---|
| Test | 3310.25 | 5508.58 | Test | 138.24 | 1321.58 |
| Ctrl | 612.87 | 26873.00 | Ctrl | 6.25 | 932.93 |

Example 5

Test of Lower Concentration of Composition on TNF-α Production by LPS-Stimulated Human Monocytes Test of the composition used in Example 4 on TNF-α production by LPS-stimulated human monocytes was undertaken, but at lower concentrations.

All other experimental procedures were identical to those used in Example 4.

Figure 5:
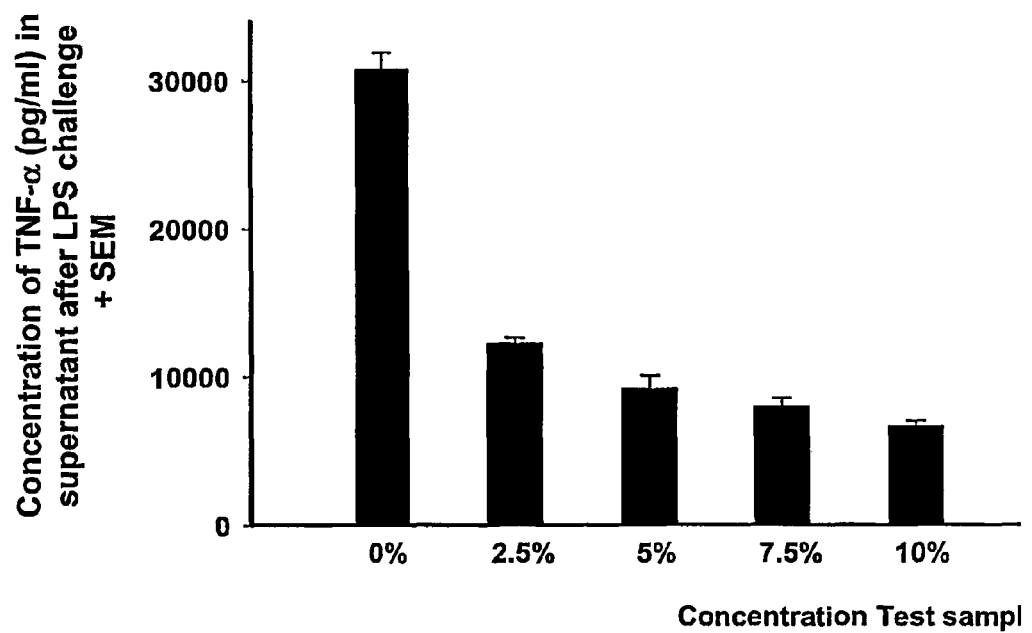
FIG. 5 shows the effect of reduced concentrations of one form of the composition of the present invention (TEST SAMPLE) comprising zinc chloride, glycine and trypsinised protein on the TNF-α production by LPS-stimulated human monocytes.

Table 9 and FIG. 5 show the results.

The conclusions that can be drawn from these results are that the TNF-alpha reducing effect of the test sample is dependent on the dosage, further supporting the outcomes of Example 1, i.e. that LPS-induced TNF-alpha secretion is inhibited by the test composition.

TABLE 9

| Groups | Average (pg/mL) | SEM |
|---|---|---|
| Test 10% | 6627.10 | 363.07 |
| Test 7.5% | 7953.37 | 579.38 |
| Test 5.0% | 9138.62 | 945.71 |
| Test 2.5% | 12211.49 | 412.64 |
| Ctrl | 30723.52 | 1140.03 |

Example 6

Titration of the Effect of Different Concentrations of Composition

Elutriated monocytes were incubated for 24 h with a checker-board pattern of test composition (10%, 5%, 2.5% & 0%) as used in Example 4 with various concentrations of FCS (10%, 5%, 1% and 0%). TNF-α was measured by ELISA in the culture supernatants as described above in Example 4.

Figure 6:
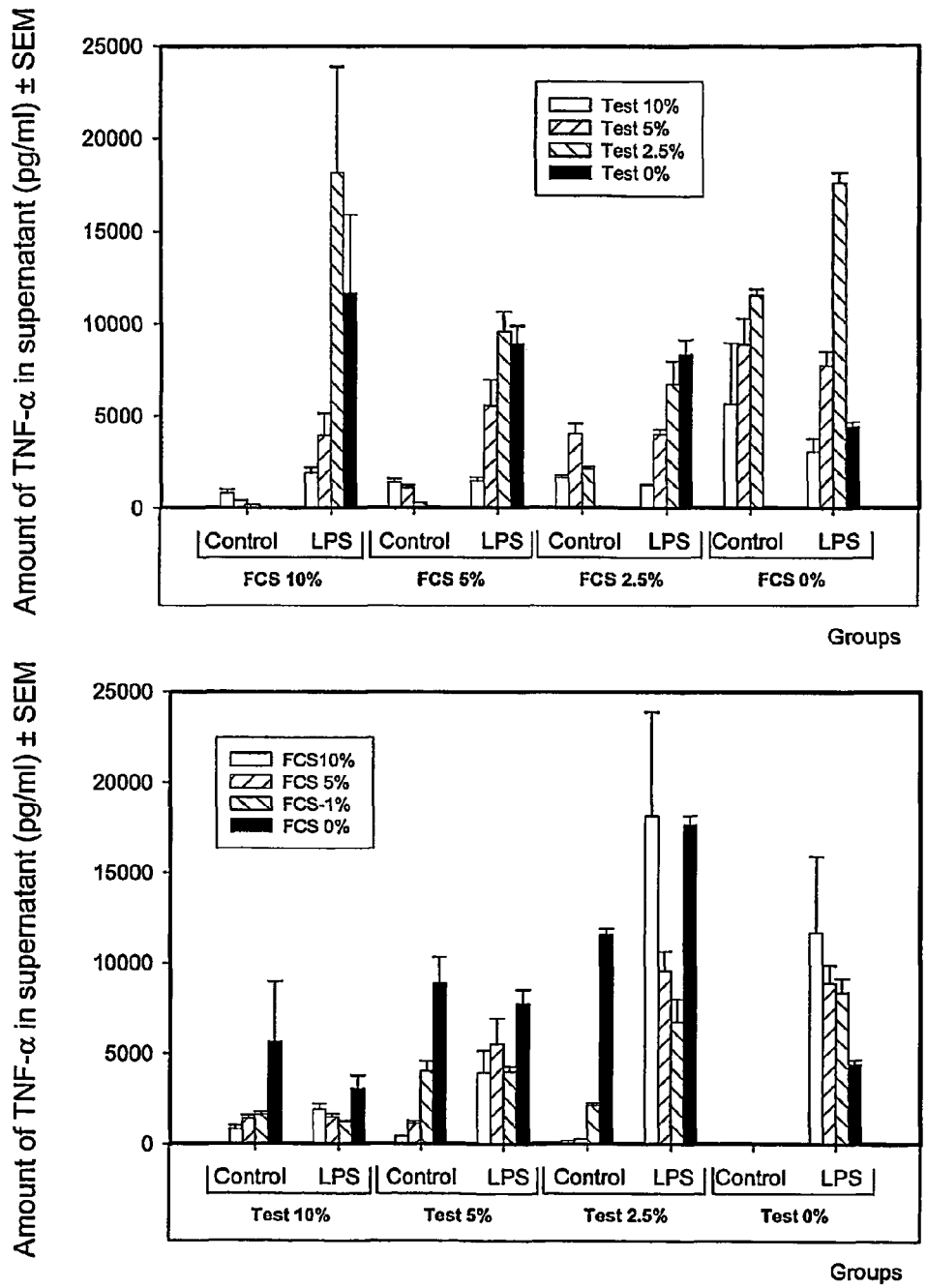
FIG. 6 shows the titration of the effect of different concentrations of the composition of the invention. The purpose was to demonstrate that TEST SAMPLE does not compete with the FCS which is being used in the culture medium.

Results are shown in Table 10 and FIG. 6.

The conclusions that can be drawn from these results are that the test sample does not compete in inhibiting TNF-alpha secretion with the FCS.

TABLE 10

| Av pg/mL | Control | LPS | SEM | Control | LPS |
|---|---|---|---|---|---|
| Test 10%/FCS-10% | 823.17 | 1919.78 | Test 10%/FCS-10% | 205.20 | 300.87 |
| Test 10%/FCS-5% | 1417.08 | 1484.48 | Test 10%/FCS-5% | 184.84 | 178.36 |
| Test 10%/FCS-1% | 1647.46 | 1273.60 | Test 10%/FCS-1% | 125.46 | 20.42 |
| Test 10%/FCS-0% | 5667.25 | 3059.38 | Test 10%/FCS-0% | 3320.00 | 719.32 |
| Test 5%/FCS-10% | 402.75 | 3961.06 | Test 5%/FCS-10% | 40.86 | 1191.91 |
| Test 5%/FCS-5% | 1123.04 | 5544.84 | Test 5%/FCS-5% | 134.77 | 1394.17 |
| Test 5%/FCS-1% | 4037.54 | 4020.51 | Test 5%/FCS-1% | 535.61 | 271.60 |
| Test 5%/FCS-0% | 8899.82 | 7748.21 | Test 5%/FCS-0% | 1411.18 | 774.46 |
| Test 2.5%/FCS-10% | 172.99 | 18144.74 | Test 2.5%/FCS-10% | 12.95 | 5740.39 |
| | 289.20 | 9552.10 | Test 2.5%/FCS-5% | 5.41 | 1102.56 |
| Test 2.5%/FCS-1% | 2139.26 | 6752.15 | Test 2.5%/FCS-1% | 117.41 | 1254.98 |
| Test 2.5%/FCS-0% | 11552.74 | 17645.83 | Test 2.5%/FCS-0% | 328.99 | 504.27 |

TABLE 10-continued

| Av pg/mL | Control | LPS | SEM | Control | LPS |
|---|---|---|---|---|---|
| Test 0%/FCS-10% | 93.50 | 11675.28 | Test 0%/FCS-10% | 5.63 | 4217.03 |
| Test 0%/FCS-5% | 99.80 | 8879.63 | Test 0%/FCS-5% | 7.12 | 989.86 |
| Test 0%/FCS-1% | 101.16 | 8374.13 | Test 0%/FCS-1% | 1.85 | 779.93 |
| Test 0%/FCS-0% | 104.32 | 4422.27 | Test 0%/FCS-0% | 2.36 | 251.71 |

Example 7

Aqueous Non-Radioactive Proliferation Assay

In order to show that the compositions of the present invention do not disturb the metabolism of cells in vitro and, thus, the TNF-alpha suppressive effect is not due to a metabolism problem of the cells a non-radioactive proliferation assay was conducted.

The specific assay used was the CellTiter 96® AQ$_{ueous}$ Non-Radioactive Cell Proliferation Assay from Promega. This method is a non-radioactive alternative to the [$^3$H] thymidine incorporation cell proliferation assay. Essentially, the manufacturer's instructions were followed, but briefly, 100 μL of 5×10$^6$ K562 (human chronic myelogenous leukaemia) cells in RPMI supplemented with 5% fetal bovine serum (FBS) were added to the wells of a 96-well plate. Cells were then incubated for 20 hours at 37° C. in a humidified, 5% $CO_2$ atmosphere. The medium was then exchanged and allowed to equilibrate for 1 hour, then 20 μL of a solution comprising (3-(4,5-dimethylthiazol-2-yl)-5-(3-carboxymethoxyphenyl)-2-(4-sulfophenyl)-2H-tetrazolium, inner salt; (MTS) and phenazine methosulfate (PMS) was added to each well. A 0 hr absorbance reading at 490 nm was taken immediately and then absorbance was measured every hour thereafter. Readings at 21 and 45 hours after the addition of the MTS/PMS solution were also taken.

Figure 7:
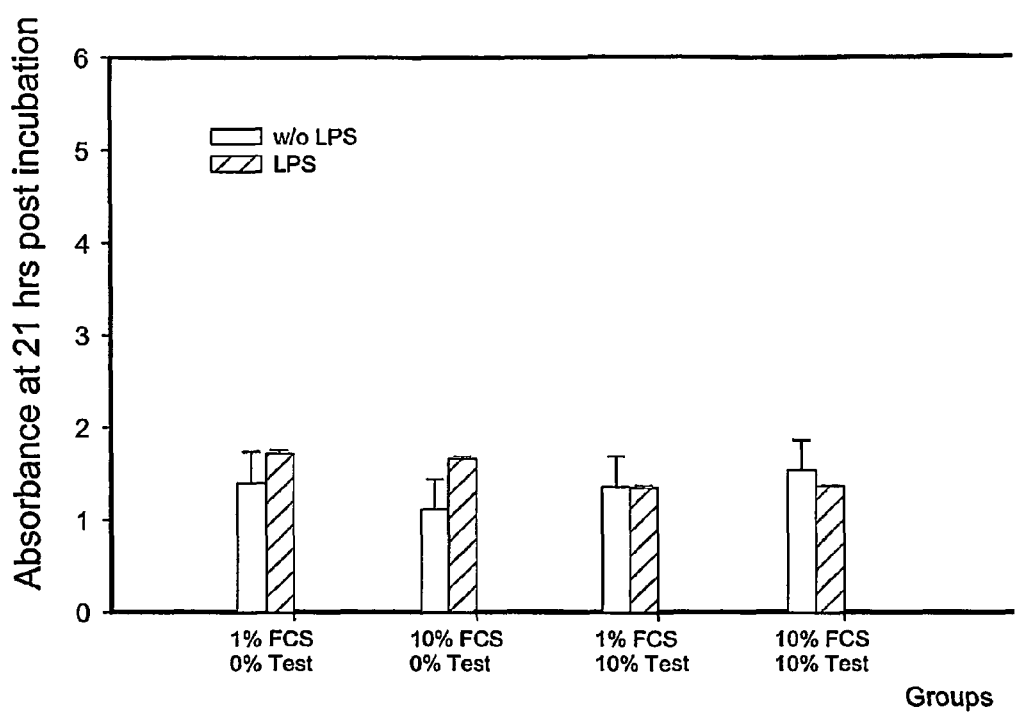
FIG. 7 shows the effect of the composition on the metabolism of cells in vitro, with or without LPS challenge, on a non-radioactive proliferation assay (CellTiter 96® AQ$_{ueous}$ Assay). The purpose was to demonstrate that the test composition does not reduce the metabolism of the cells.

It can be seen from FIG. 7 that these cells do not proliferate. The dye wears off with a higher metabolism, which is reflected in higher absorbance (y-axis). The data from TL-treated+LPS challenged cells shows that the test samples were slightly less metabolically active than the controls, but at the same time TNF-alpha secretion was suppressed. These data are not totally unexpected as the need for a higher metabolism when compared with the untreated+LPS-challenged cells would be less for these cells. Non-LPS-challenged cells do not differ in metabolism, whether treated with the test compositions or not.

From these data it can be concluded that the inhibition of TNF-alpha secretion seen in Examples 4, 5, and 6, was not due to a reduction in metabolic functioning of the cells.

It should be noted that in all experiments supra the viability of cells, both test and control, were assessed visually. In all instances the cells exposed to test composition were viable as indicated by typical cell spreading over the culture vessel. The cell spreading noted was the same as the cell spreading noted fro the non-challenged/non-treated cells.

Example 8

TNF-Receptor Binding

Figure 8:
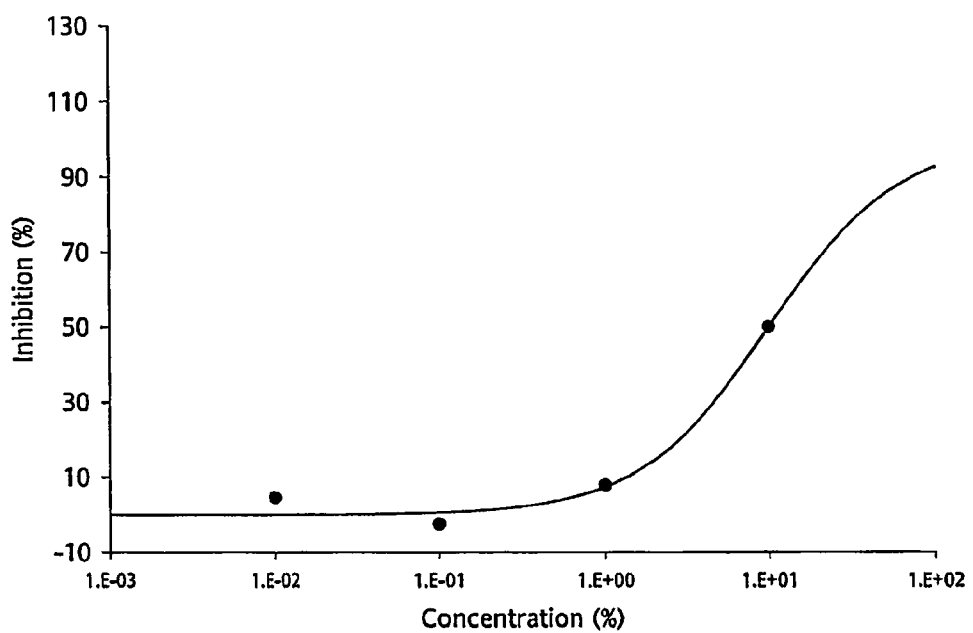
FIG. 8 shows that the test sample was able to inhibit the binding of TNF-α to its receptor.

The composition shown in Example 2 was found to inhibit binding of TNF-α to its receptor as assessed with human U937 cells (see FIG. 8). The $K_i$ is 7.17% μg/ml ($IC_{50}$: 10%) of the test sample solution comprising zinc chloride, glycine, and trypsinised protein. Displacing TNFalpha from its receptor is a means of modulation the secretion of TNF-alpha and subsequently triggered cytokine cascades.

Example 9

TACE Inhibition

TNF-α is initially expressed on the cell surface as a 26-kDa, type II trans-membrane pro-form. The membrane-bound pro-TNF-α can then be cleaved between Ala-76 and Val-77 by a Zn-metalloprotease, TNF-α converting enzyme (TACE), resulting in the formation of the 17-kDa, mature, soluble cytokine.

TACE belongs to the family of metalloprotease disintegrins (also known as ADAM or MDC family), which are modular transmembrane proteins with a Zinc-dependent catalytic domain. Metalloprotease disintegrins are synthesized as inactive precursors containing a prodomain that blocks the activity of the catalytic domain. TACE is the predominant protease responsible for the generation of soluble TNF-α. T cells derived from $TACE^{\Delta Zn/\Delta Zn}$ knockout mice have a 90% reduction in their ability to process pro-TNF-α. Levels of TACE protein and its enzymatic activity in the synovial tissue of patients with RA are significantly higher than those of patients with osteoarthritis. Therefore, TACE inhibitors, which inhibit the processing of pro-TNF-α on the plasma membrane, represent an appealing alternative to the neutralization of TNF-α by biological agents.

TACE is also required for the activation of the receptor for the epidermal growth factor (EGFR) in vivo and for the development of tumors in nude mice, indicating a crucial role of TACE in tumorigenesis. In agreement with this view, TACE is dramatically over-expressed in the majority of mammary tumors analyzed. Collectively, this evidence points to TACE as a promising target of anti-tumor therapy.

The composition described in Example has been shown to reduce the release of TNF-α secretion by monocytes upon an LPS challenge. This indicates that the composition of the invention is an inhibitor of TACE.

Figure 9:
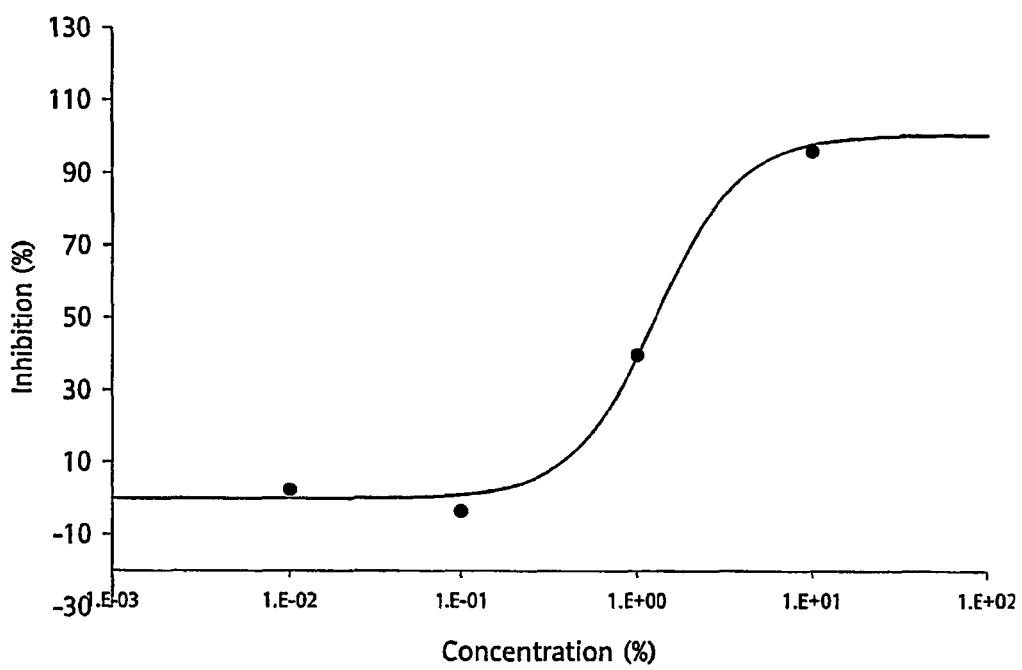
FIG. 9 shows that TACE is inhibited 72% by 10% of the test solution comprising zinc chloride, glycine and trypsinised protein.

A direct measurement of human TACE activity in human recombinant insect Sf21 cells revealed that the test composition (zinc chloride as trace element) inhibited the TACE activity with an $IC_{50}$ of 1.28% of protein of the test composition (FIG. 9). In conclusion this data shows that the test composition modulates cytokines also via TACE.

Example 10

Chemokine CCR Receptors

The allergic airway inflammation of asthma is characterized by the recruitment of eosinophils from the blood into the airways. Eosinophils are able to contribute to the inflammatory response by release of mediators that induce bronchoconstriction, increased microvascular permeability, and mucus formation, and through the release of toxic granule contents that cause tissue damage in the lungs. Eosinophils may further contribute to the inflammatory response through their abilities to function as antigen-presenting cells.

CCR1 is closely related to CCR3, which is the main chemokine receptor to regulate eosinophil accumulation. CCR1 is expressed by basophils, monocytes, and memory T cells.

15-20% of people have high levels of CCR1 expressed by eosinophils. Eosinophils from these donors are highly responsive to CCL3/macrophage-inflammatory protein MIP-1α.

CCL3 expression is increased in human asthmatic lung. These findings suggest that CCR1 or CCR3 block or antagonism can be therapeutic in asthmatic conditions.

Also in severe respiratory virus infections, the associated inflammation through the MIP-1α/CCR1 pathway should be addressed with an antagonistic therapy. A CCR1 antagonist should in this case be used in conjunction with anti-viral strategies. For instance, in mice an infection with the natural rodent pathogen pneumonia virus was limited by the antiviral agent ribavirin. However, the antiviral therapy had no impact on morbidity and mortality when the antiviral agent was not accompanied by the immunomodulator Met-RANTES to counteract the MIP-1 mediated inflammation.

RA patients treated with a potent and selective antagonist of CCR1 were reported to show a clear reduction in synovial inflammation.

Figure 10:
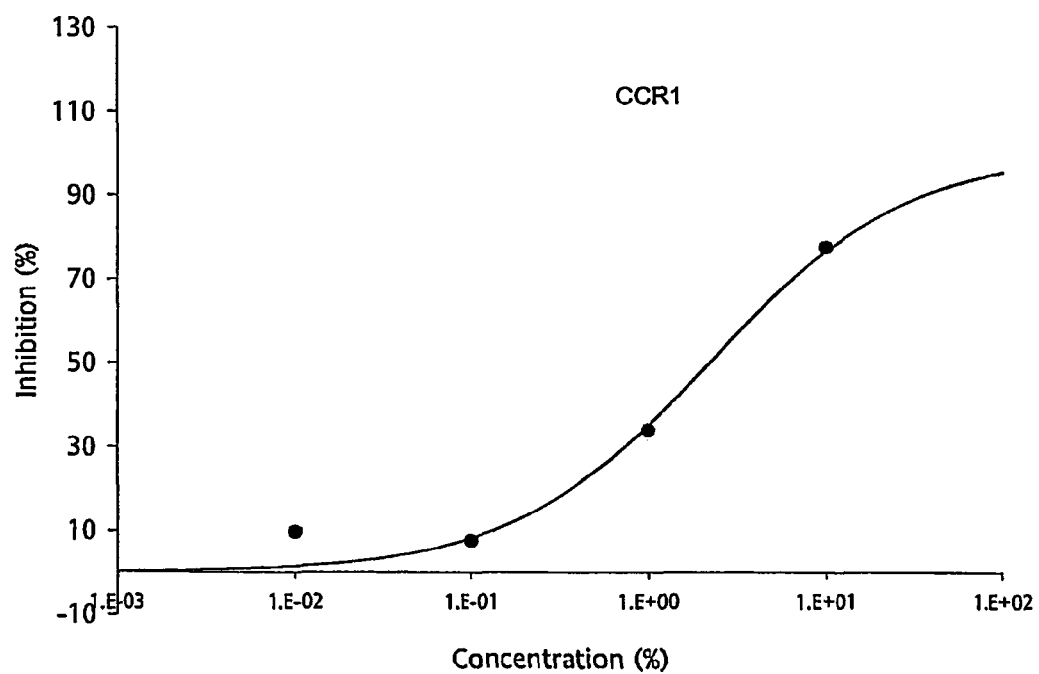
FIG. 10 shows that the test composition comprising zinc chloride, glycine and trypsinised protein can replace the chemokine/cytokine MIP-1alpha from its receptor CCR1.

The composition described in Example 2 binds to the human CCR1 receptor, assessed by competition with [$^{125}$I] MIP-1α with a $K_i$ of 1.02% ($IC_{50}$=2.21%) of the test composition with zinc chloride as only trace element (see FIG. 10). This demonstrates that a broad efficacy of the test composition in affecting the cytokine modulation.

Example 11

Caspase Inhibition

The interleukin-1b converting enzyme ICE, now renamed caspase-1, is a cysteine endoprotease. The enzyme directly cleaves pro-IL-1 to mature cytokine IL-1b that is released into the extracellular environment. To date more than ten caspases are known. Much evidence has been accumulated to suggest that inhibition of caspase-1 can directly lead to a lowering of IL-1b in vitro and in vivo. This effect has been correlated with efficacy in ameliorating the symptoms of inflammation in many models of inflammatory diseases in animals and humans. Clinical trials data on pralnacasan and VX-765 have shown that caspase-1 inhibitors in general, can be effective for the treatment rheumatoid arthritis, osteoarthritis and psoriasis.

Figure 11:
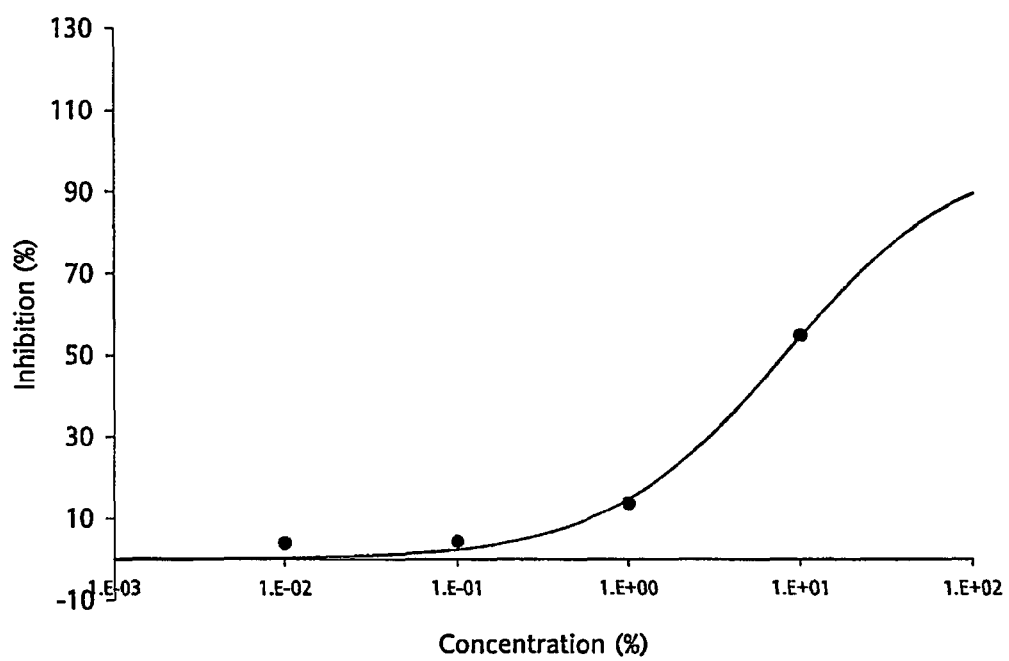
FIG. 11 shows that the test composition comprising zinc chloride, glycine and trypsinised protein can inhibit caspase 1, an enzyme that affects the secretion of the cytokine IL1beta.

We found that the composition described in Example 2 was capable of inhibiting the human Caspase 1 with an $IC_{50}$ of 8.11% of the test composition (see FIG. 11), demonstrating an additional means of modulating cytokines with the test composition with zinc chloride as trace element.

Example 12

TNF IL1Beta

As described in Example 4, monocyte cultures were stimulated with 500 ng/ml LPS from *E. coli* 0111:B4 (Sigma-Aldrich) in the presence of 10% FCS and 0%, 10% Test sample 2 (test composition comprising all ingredients in example 1), and 10% test sample 3 (comprising Zinc chloride, magnesium sulfate heptahydrate, cupric sulphate pentahydrate, glycine, trypsinised protein). All treatments were conducted in triplicate and cultures were incubated under humidified conditions for 24 hours at 37° C. in 5% $CO_2$.

Following 24 hour incubation, culture media samples were collected and cells and particulates were removed by centrifugation. Clarified supernatants were stored at −70° C. and assayed in batch. The concentration of TNF-α and IL1β in culture supernatants was measured using a commercial cytokine ELISA set (BD Biosciences) according to the manufacturer's instructions. TNF-α concentrations in the culture media were derived from a standard curve (125-8000 pg/ml).

The detection system selected for these ELISAs was time-resolved fluorescence (TRF) with europium. TRF has been used in many biological systems as a means to reduce background fluorescence and increase sensitivity. Lanthanides such as europium exhibit a large Stokes shift, with excitation occurring by absorbance of UV light with emission wavelengths greater than 500 nm. Europium exhibits excitation at 340 nm and emission at 615 nm.

Figure 12:
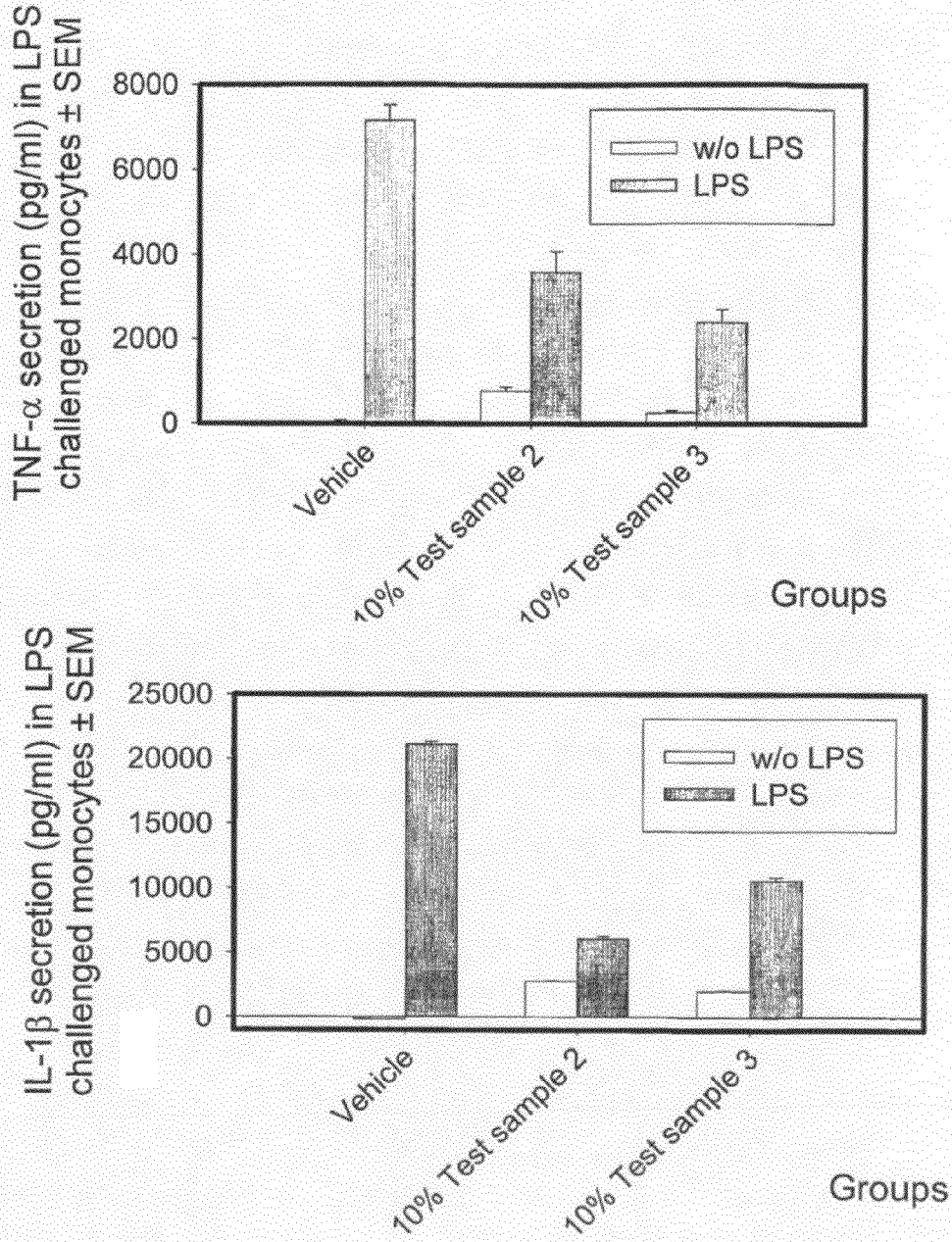
FIG. 12 shows the suppression of an LPS-induced inflammatory response of cultured human monocytes by pharmacological treatment. The treatments were done in triplicate, and the TNF-α levels (left panel) as well as the IL1β levels (right panel) were measured at 24 hours after treatment with 0%, 10% Test composition comprising all ingredients in example 1 (test sample 2), and 10% test sample 3, comprising Zinc chloride, magnesium sulfate heptahydrate, cupric sulphate pentahydrate, glycine, trypsinised protein in the aqueous active form. Means and standard errors of the means for the concentration of TNF-α and IL1β in the supernatants of the different treatment groups are depicted.

As shown in FIG. 12 data was collated and mean and standard error of mean (SEM) were calculated for each experimental condition. Monocyte TNF-α and IL1β secretion into culture media was expressed as pg/ml.

Example 13

Preparation of an Analgesic and Anti-Inflammatory Composition

Figure 13:
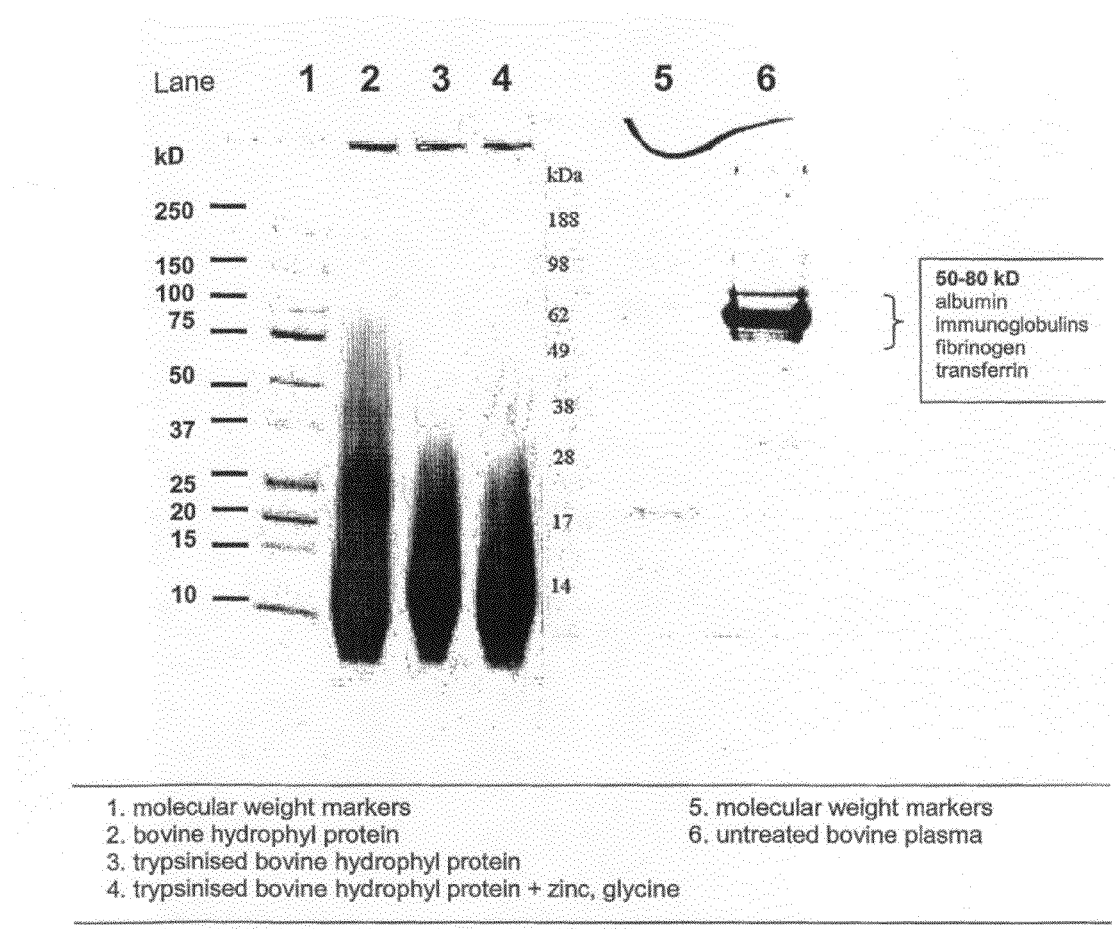
FIG. 13 (left panel) shows a 10-20% SDS-PAGE Tricine gradient gel. Proteins were stained with Coomassie blue. Lane 1 contains molecular weight markers. Lanes 2 shows bovine soluble protein prior to trypsinisation and lane 3 and 4 after trypsinisation, as indicated. This gel shows that the majority of proteins with aromatic rings in the preparation are in a size range less than 50 kilodaltons.
Figure 14:
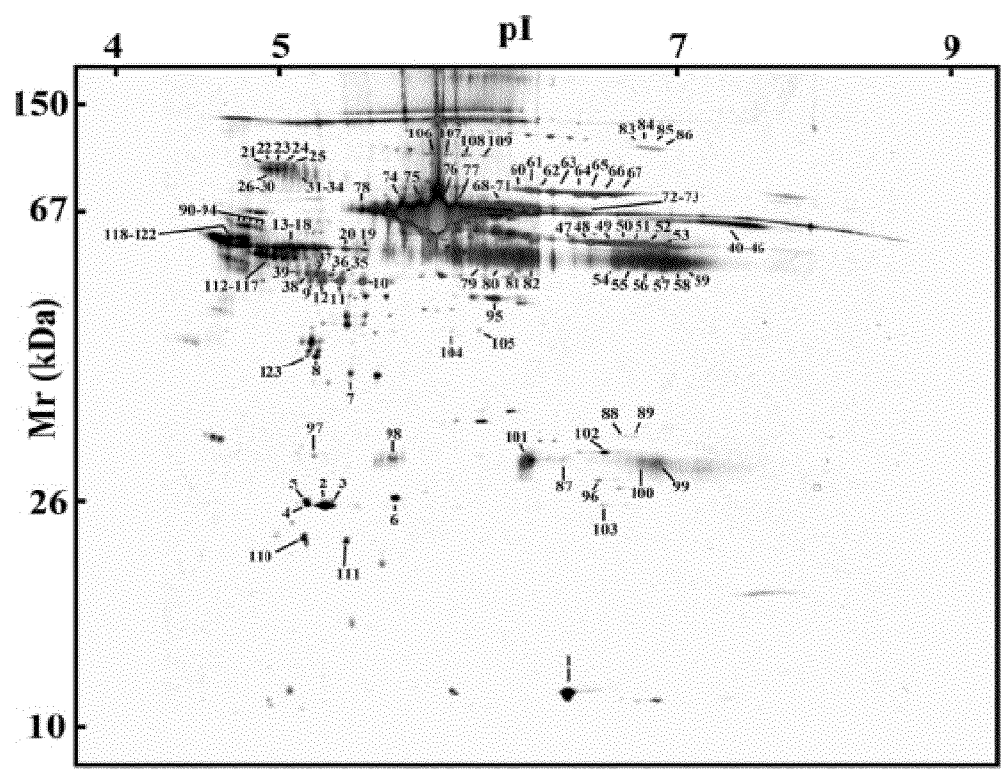
FIG. 14 shows bovine plasma by 2-D electrophoresis map using the method of Talamo et al., 2003, *Proteomics*, 3:440-460.
Figure 15:
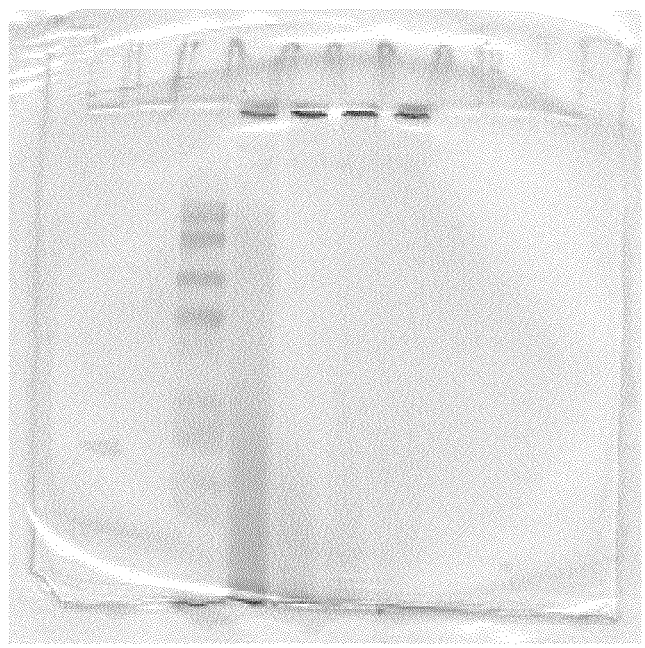
FIG. 15 shows an 8% SDS-PAGE Tris-glycine gel. Lanes are as in the left section of FIG. 1. This gel confirms that the majority of proteins with aromatic rings in the preparation are in a size range less than 50 kilodaltons.

A composition as described in Example 1 prepared. FIGS. 13 to 16 show the soluble plasma protein fragments obtained by this method. In FIG. 13, the major protein bands apparent in untreated plasma separated by SDS-PAGE are 50-80 kDa in size (Lane 6) Proteomic analysis of these bands identified them as consisting mainly of albumin, immunoglobulins, fibrinogen and transferrin (FIG. 14).

Figure 16:
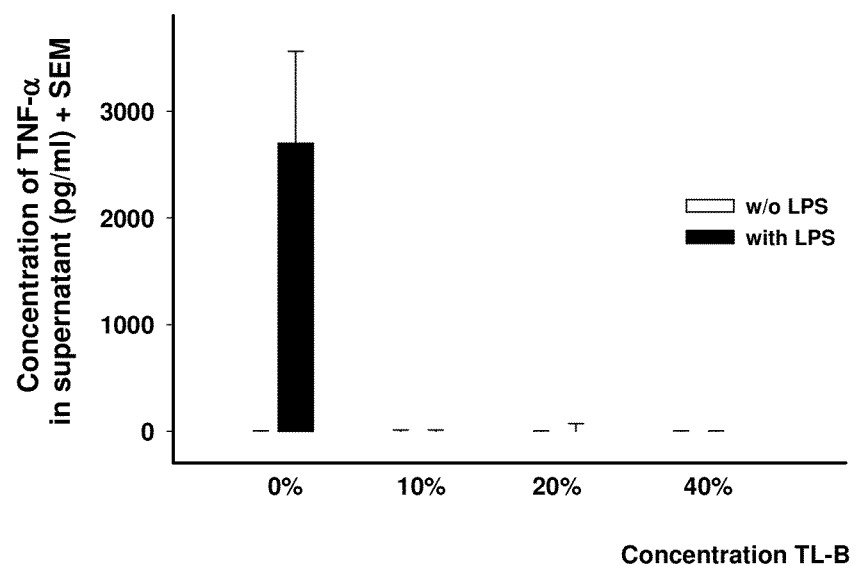
FIG. 16 shows the effect of one form of the composition of the present invention comprising zinc chloride, glycine and trypsinised protein on the TNF-α production by LPS-stimulated human monocytes.

In contrast, the plasma protein before protease treatment consists mainly of polypeptides smaller than 50 kDa (FIG. 13. Lane 2), while after trypsinisation the soluble plasma protein fragments are reduced to molecular weights of less than 25 kDa (10-20% tricine gradient gel, FIG. 13. Lanes 3, 4). FIG. 16 shows the same samples on an 8% trisglycine gel.

Example 14

Test of Composition on TNF-α Production by LPS-Stimulated Human Monocytes

The soluble plasma test composition from Example 13 was assayed for its ability to affect TNF-α levels by the method disclosed in Example 3.

In the present experiment, the soluble plasma test composition described in Example 13 was mixed with zinc chloride (0.006157 g/L) and glycine (0.1965 g/L). This test composition is also known as TL-B.

The concentrations of test composition used were 40% (200 μL); 20% (100 μL); 10% (50 μL); and 0%. The control was LPS (500 ng/mL) and there were 3 repeats.

Results were collated and mean and standard error of the mean (SEM) were calculated for each experimental condition. Monocyte TNF-α secretion into culture media was expressed as pg/ml. The effects of LPS and test composition treatments on the concentration of TNF-α in the supernatant were assessed by a Treat by LPS (with the levels LPS and no LPS) analysis of variance (ANOVA), supplemented with Fisher's least significant difference (LSD) post hoc comparisons. The factor Treat had levels no treat, 10, 20, and 40% of the test composition. A difference between groups was considered as statistically reliable if the associated probability (p value) was below 0.05. Table 11 together with FIG. 16 shows the results.

TABLE 11

| Av pg/mL | w/o LPS | with LPS | SEM | w/o LPS | with LPS |
|---|---|---|---|---|---|
| Test 40% | 0 | 0 | 40% | 3.28 | 1.25 |
| Test 20% | 0 | 0 | 20% | 2.17 | 72.18 |
| Test 10% | 0 | 0 | 10% | 11.01 | 12.88 |
| Test 0% | 0 | 2700.23 | 0% | 3.72 | 861.07 |

SEM: Standard Error of the Mean

Statistical analysis: The LPS challenge produced a large quantity of TNF-α secretion in untreated cells at 24 hours after incubation (LPS: $F_{1,16}=10.17$, $p<0.01$). The treatments affected the TNF-α response to the LPS challenge (Treat: $F_{3,16}$ 9.69, $p<0.001$; Treat by LPS: $F_{3,16}=9.19$, $p<0.001$). Post hoc comparisons revealed that LPS-challenged, TL-B treated cells produced less TNF-α secretion than the LPS-challenged, untreated cells. Unchallenged cells did not produce measurable amounts of TNF-α with any of the treatments. TL-B treatment resulted in suppression of TNF-α to a level indistinguishable from unchallenged cells.

The conclusions that can be drawn from the results are that the soluble plasma test composition decreases LPS-induced TNF-alpha secretion in human monocytes, indicating efficacy in inhibiting inflammatory responses.

Example 15

Effect of Soluble Plasma Test Composition on TNF-α Production by LPS-Stimulated Human Monocytes This experiment was essentially a repeat of the experiment described in Example 14, with the only difference being the soluble plasma test composition in Example 13 was mixed with a metal-containing solution contained only copper sulphate (0.00262 g/L).

Figure 17:
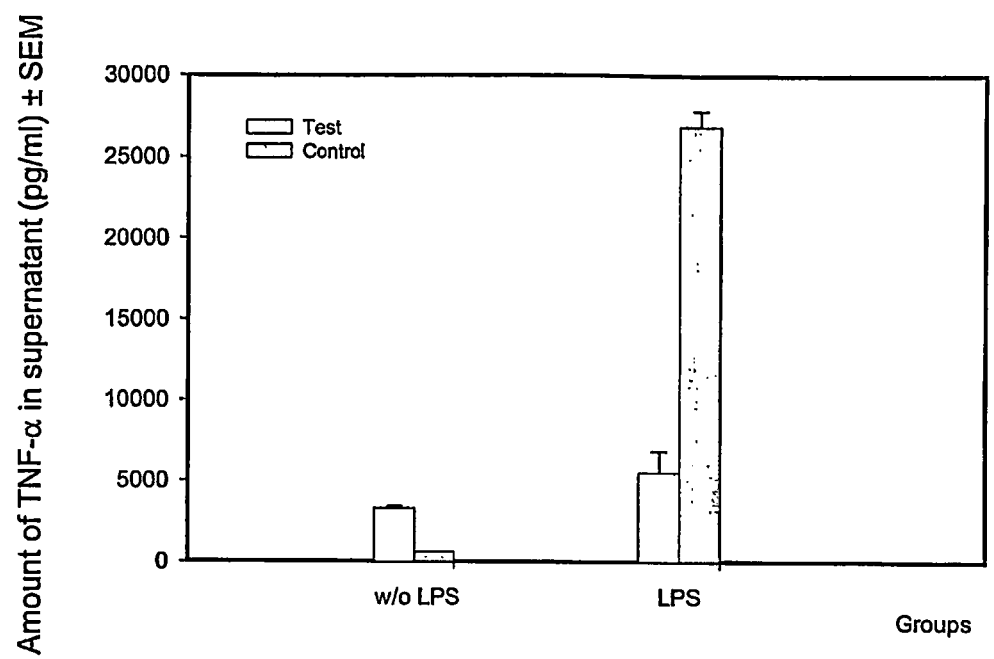
FIG. 17 shows the effect of the composition of the present invention, containing copper as the metal-containing solution, on the TNF-α production by LPS-stimulated human monocytes.

Table 12 and FIG. 17 show the results.

The conclusions that can be drawn from these results are that the soluble plasma test composition inhibits the inflammatory response of human monocytes to an LPS challenge.

TABLE 12

| Av pg/mL | Ctrl | LPS | SEM | Ctrl | LPS |
|---|---|---|---|---|---|
| Test | 3310.25 | 5508.58 | Test | 138.24 | 1321.58 |
| Ctrl | 612.87 | 26873.00 | Ctrl | 6.25 | 932.93 |

Example 16

Test of Lower Concentration of Soluble Plasma Test Composition on TNF-α Production by LPS-Stimulated Human Monocytes Test of the soluble plasma test composition used in Example 14 on TNF-α production by LPS-stimulated human monocytes was undertaken, but at lower concentrations.

All other experimental procedures were identical to those used in Example 14.

Figure 18:
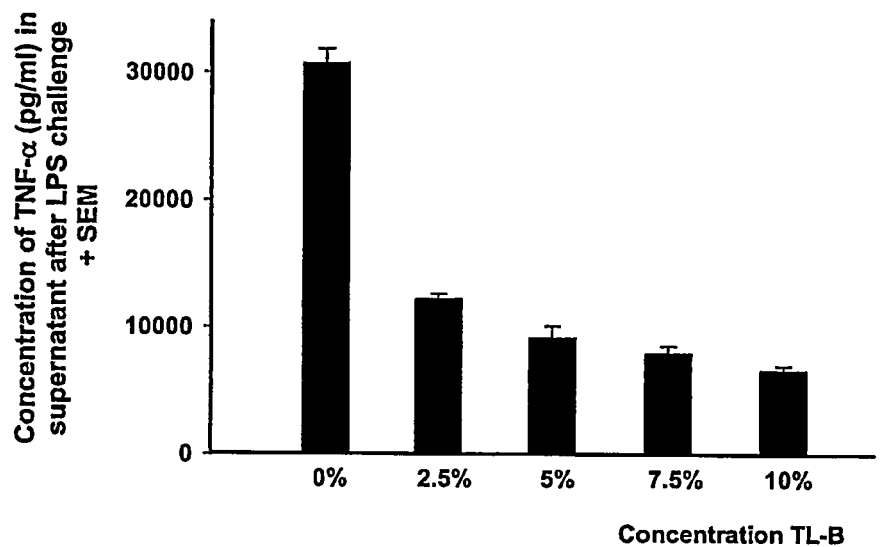
FIG. 18 shows the effect of reduced concentrations of one form of the composition of the present invention comprising zinc chloride, glycine and trypsinised protein on the TNF-α production by LPS-stimulated human monocytes.

Table 13 and FIG. 18 show the results.

The conclusions that can be drawn from these results are that the anti-inflammatory effect of the soluble plasma test composition is dependent on the dosage, further supporting the outcomes of Example 14, i.e. that LPS-induced TNF-alpha secretion is inhibited by the test composition.

TABLE 13

| Groups | Average (pg/mL) | SEM |
|---|---|---|
| Test 10% | 6627.10 | 363.07 |
| Test 7.5% | 7953.37 | 579.38 |
| Test 5.0% | 9138.62 | 945.71 |
| Test 2.5% | 12211.49 | 412.64 |
| Ctrl | 30723.52 | 1140.03 |

Example 17

Titration of the Effect of Different Concentrations of Soluble Plasma Test Composition Elutriated monocytes were incubated for 24 h with a checker-board pattern of soluble plasma test composition (10%, 5%, 2.5% & 0%) as used in Example 14 with various concentrations of FCS (10%, 5%, 1% and 0%). TNF-α was measured by ELISA in the culture supernatants as described above in Example 14.

Figure 19:
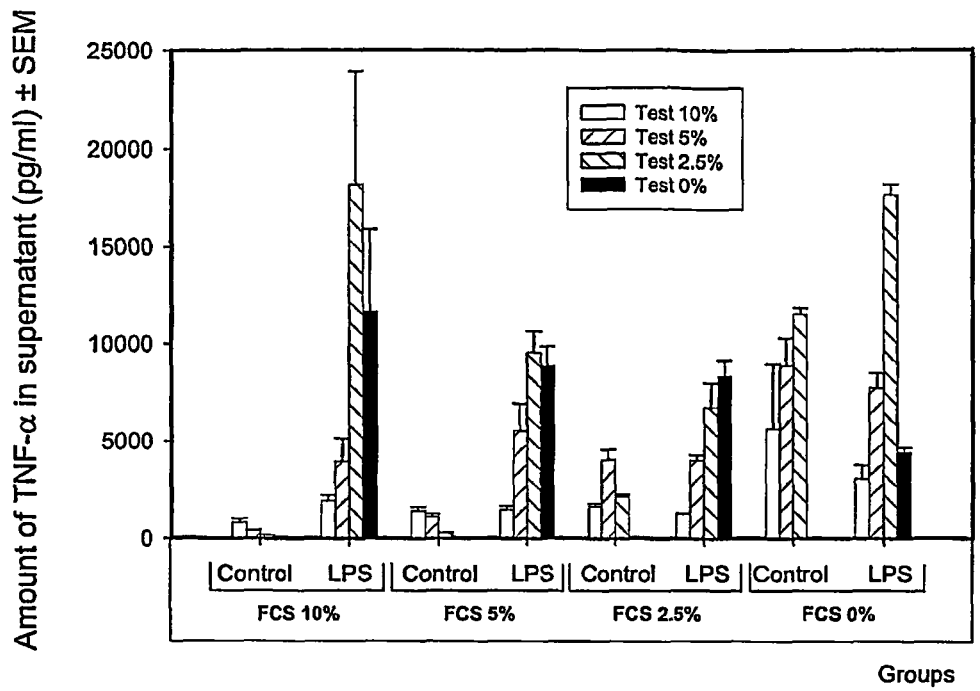
FIG. 19 shows the titration of the effect of different concentrations of the composition of the present invention. The purpose was to demonstrate that the composition of the present invention comprising zinc chloride, glycine and trypsinised protein does not compete with the FCS which is being used in the culture medium.
Figure 19:
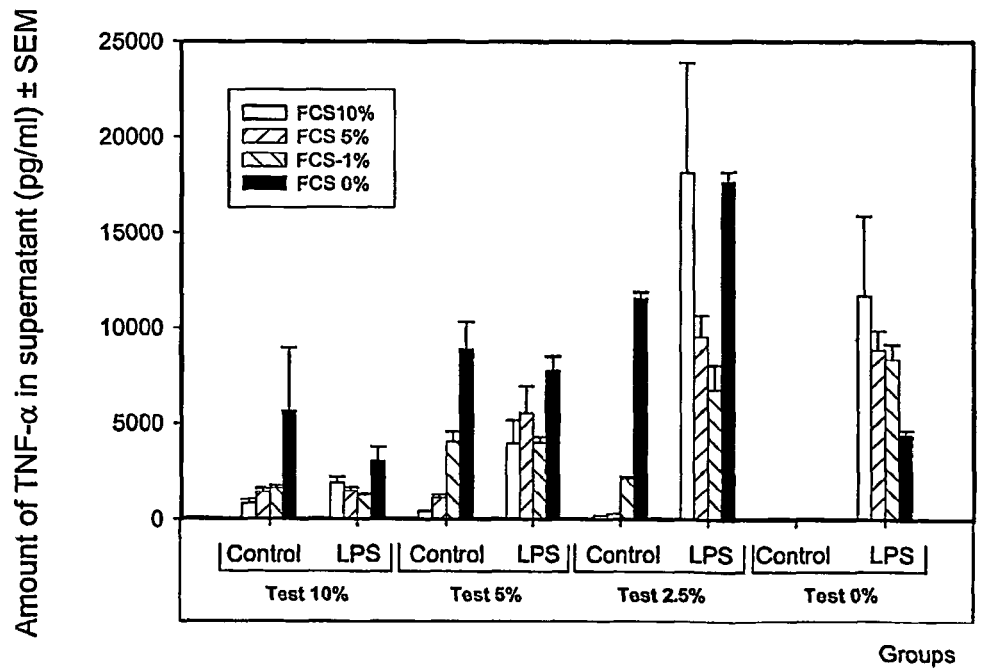

Results are shown in Table 14 and FIG. 19.

The conclusions that can be drawn from these results are that the soluble plasma test composition does not compete in inhibiting TNF-alpha secretion with the FCS.

TABLE 14

| Av pg/mL | Control | LPS | SEM | Control | LPS |
|---|---|---|---|---|---|
| Test 10%/FCS-10% | 823.17 | 1919.78 | Test 10%/FCS-10% | 205.20 | 300.87 |
| Test 10%/FCS-5% | 1417.08 | 1484.48 | Test 10%/FCS-5% | 184.84 | 178.36 |
| Test 10%/FCS-1% | 1647.46 | 1273.60 | Test 10%/FCS-1% | 125.46 | 20.42 |
| Test 10%/FCS-0% | 5667.25 | 3059.38 | Test 10%/FCS-0% | 3320.00 | 719.32 |
| Test 5%/FCS-10% | 402.75 | 3961.06 | Test 5%/FCS-10% | 40.86 | 1191.91 |
| Test 5%/FCS-5% | 1123.04 | 5544.84 | Test 5%/FCS-5% | 134.77 | 1394.17 |
| Test 5%/FCS-1% | 4037.54 | 4020.51 | Test 5%/FCS-1% | 535.61 | 271.60 |
| Test 5%/FCS-0% | 8899.82 | 7748.21 | Test 5%/FCS-0% | 1411.18 | 774.46 |
| Test 2.5%/FCS-10% | 172.99 | 18144.74 | Test 2.5%/FCS-10% | 12.95 | 5740.39 |
|  | 289.20 | 9552.10 | Test 2.5%/FCS-5% | 5.41 | 1102.56 |
| Test 2.5%/FCS-1% | 2139.26 | 6752.15 | Test 2.5%/FCS-1% | 117.41 | 1254.98 |
| Test 2.5%/FCS-0% | 11552.74 | 17645.83 | Test 2.5%/FCS-0% | 328.99 | 504.27 |
| Test 0%/FCS-10% | 93.50 | 11675.28 | Test 0%/FCS-10% | 5.63 | 4217.03 |
| Test 0%/FCS-5% | 99.80 | 8879.63 | Test 0%/FCS-5% | 7.12 | 989.86 |
| Test 0%/FCS-1% | 101.16 | 8374.13 | Test 0%/FCS-1% | 1.85 | 779.93 |
| Test 0%/FCS-0% | 104.32 | 4422.27 | Test 0%/FCS-0% | 2.36 | 251.71 |

Example 18

Aqueous Non-Radioactive Proliferation Assay

In order to show that the soluble plasma test composition of Example 14 does not disturb the metabolism of cells in vitro and, thus, the TNF-α suppressive effect is not due to a metabolism problem of the cells a non-radioactive proliferation assay was conducted.

The specific assay used was the CellTiter 96® AQ$_{ueous}$ Non-Radioactive Cell Proliferation Assay from Promega. This method is a non-radioactive alternative to the [$^3$H] thymidine incorporation cell proliferation assay. Essentially, the manufacturer's instructions were followed, but briefly, 100 µL of 5×10$^6$ K562 (human chronic myelogenous leukaemia) cells in RPMI supplemented with 5% fetal bovine serum (FBS) were added to the wells of a 96-well plate. Cells were then incubated for 20 hours at 37° C. in a humidified, 5% CO$_2$ atmosphere. The medium was then exchanged and allowed to equilibrate for 1 hour, then 20 µL of a solution comprising (3-(4,5-dimethylthiazol-2-yl)-5-(3-carboxymethoxyphenyl)-2-(4-sulfophenyl)-2H-tetrazolium, inner salt; (MTS) and phenazine methosulfate (PMS) was added to each well. A 0 hr absorbance reading at 490 nm was taken immediately and then absorbance was measured every hour thereafter. Readings at 21 and 45 hours after the addition of the MTS/PMS solution were also taken.

Figure 20:
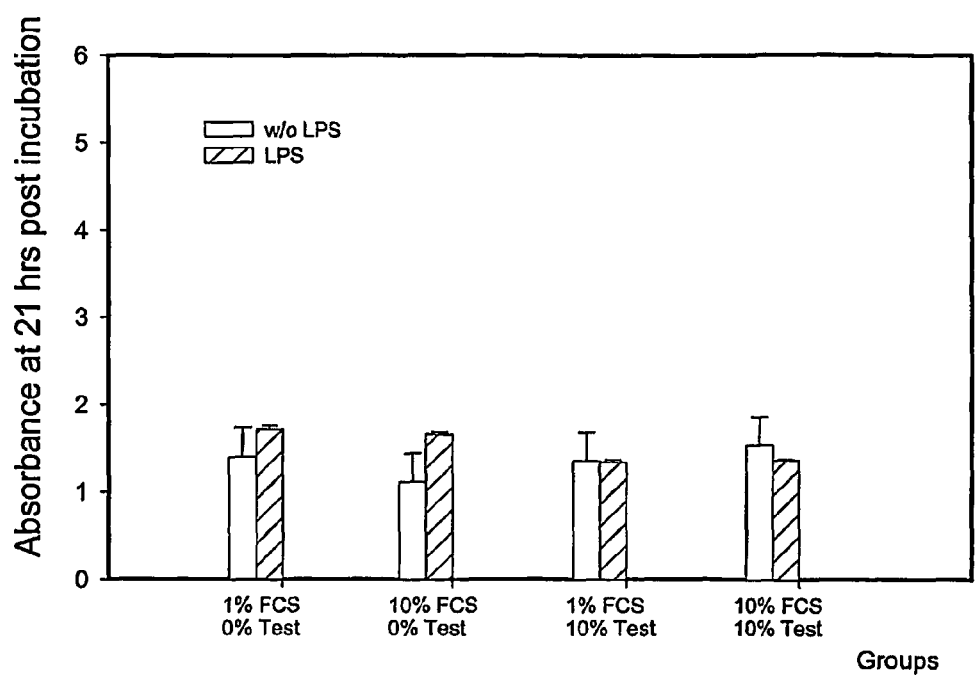
FIG. 20 shows the effect of the composition on the metabolism of cells in vitro, with or without LPS challenge, on a non-radioactive proliferation assay (CellTiter 96® AQ$_{ueous}$ Assay). The purpose was to demonstrate that the test composition does not reduce the metabolism of the cells.

It can be seen from FIG. 20 that these cells do not proliferate. The dye wears off with a higher metabolism, which is reflected in higher absorbance (y-axis). The data from TL-treated+LPS challenged cells shows that the test samples were slightly less metabolically active than the controls, but at the same time TNF-alpha secretion was suppressed. These data are not totally unexpected as the need for a higher metabolism when compared with the untreated+LPS-challenged cells would be less for these cells. Non-LPS-challenged cells do not differ in metabolism, whether treated with the soluble plasma test composition or not.

From these data it can be concluded that the inhibition of TNF-α secretion seen in Examples 14, 15, and 16, was not due to a reduction in metabolic functioning of the cells.

Example 19

TNF-α Antagonism

The underlying cause of debilitating inflammatory diseases such as rheumatoid arthritis, lupus, Crohn's disease, psoriasis, and ankylosing spondylitis is still poorly understood. Despite this, drugs to alleviate the symptoms have been used for many years and include: non-steroidal anti-inflammatory drugs (NSAIDS, such as aspirin, naproxen and until recently Celebrex), corticosteroids, and disease modifying antirheumatic drugs. In the early 1990's however, it was realised that tumour necrosis factor alpha (TNF-α) is the crucial cytokine in the establishment and maintenance of inflammation in many autoimmune diseases. TNF-α, IL-1 and IL-6 are now known to be potent mediators of the immune and acute phase response caused by surgery and trauma. Their production can be reduced by steroids, nonsteroidal anti-inflammatory agents, nitric oxide and anti-inflammatory cytokines such as IL-4, IL-10 and IL-13. Interestingly some anaesthetics used in surgery can also reduce the generation of TNF-α, IL-1 and IL-6.

Antibodies to TNF-α can reduce the levels of TNF-α, and subsequently the production of IL-1b (interleukin-1b) in rheumatoid synovial cultures along with many other cytokines. This finding has led to a new generation of drugs for the treatment of these disorders. TNF-α neutralising agents are currently in the marketplace. Infliximab (Remicade®), a chimeric monoclonal antibody against TNF-α, has been approved for Crohn's disease, rheumatoid arthritis, and ankylosing spondylitis and shows promise for a variety of other diseases. Etanercept (Enbrel®) is a soluble tumour necrosis factor receptor also approved for rheumatoid arthritis, juvenile rheumatoid arthritis, psoriatic arthritis, ankylosing spondylitis and psoriasis.

The recent clinical success of anti-TNF-α agents such as the soluble TNF-α receptor and anti-TNF-α antibody has further validated TNF-α as an important therapeutic target for RA. However, despite the success of these biological agents in the treatment of RA, this class of agents has various limitations, including the requirement of parenteral injection, high cost, and the possibility of antibody formation against these agents. Synovial macrophages, a key cell population in RA, secrete TNF-α, which induces the production of proinflammatory cytokines and matrix metalloproteinases. Interestingly within 48 hr of treatment with TNF-α, a decrease in macrophage numbers was observed in the synovial fluid of RA patients, possibly suggesting a progressive feed-back loop. Treatment with TNF-α antagonists, the soluble TNF receptor (etanercept) or the TNF chimeric monoclonal antibody (infliximab), has been shown to be highly clinically efficacious and to delay joint destruction in RA. Treatment furthermore significantly increased synovial apoptosis, primarily of the monocyte/macrophage population, but not of the lymphocyte population. TNF-α blockade is an effective treatment for plaque-type psoriasis, inducing remission in about 80% of patients.

The development of further antagonists of TNF-α represents a highly desirable strategy for treating inflammatory diseases such as rheumatoid arthritis, lupus, Crohn's disease, psoriasis, and ankylosing spondylitis. Interestingly TNF-α has also been demonstrated to play a role in experimental (MPTP induced) Parkinson in monkeys.

In the brain of Parkinson patients increased levels of inflammatory cytokines like TNF-α have been reported. In TNF-α-deficient mice, cerebral ischemic lesions were less. Mice injected with a mixture of neutralizing anti-TNF and anti-CD95L antibodies 30 min after induction of stroke have been reported to show a marked decrease in both infarct volumes and mortality, an effect which was interpretated to be related to the apoptotic affect of TNF-α.

As TNF-α is known to stimulate apoptosis, antagonists may also be of interest in indications where apoptosis is involved.

Figure 21:
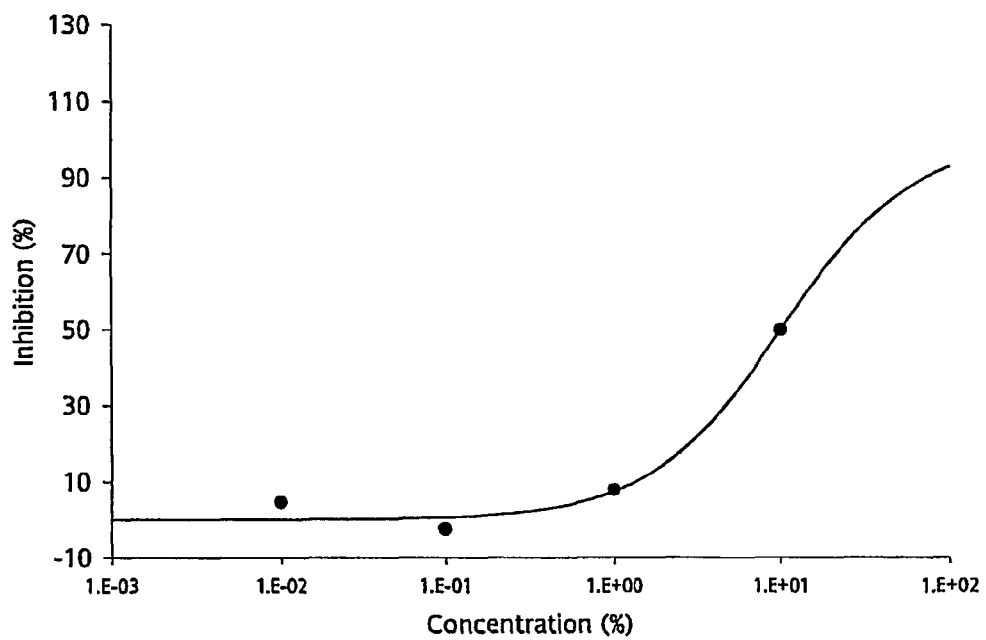
FIG. 21 shows the inhibitory effect of a soluble plasma precipitate composition comprising zinc chloride, glycine and trypsinised protein of the present invention on the radioligand binding of TNF-α to its receptor as assessed with human U937 cells. The Ki is 7.2% (IC$_{50}$: 10%) of the test sample solution. The purpose was to show that the test composition is also active in another part of the TNF-α cascade, i.e. inhibiting binding of TNF-α to the TNF receptor.

The soluble plasma test composition of the present invention was found to inhibit binding of TNF-α to its receptor as assessed with human U937 cells. The Ki was 7.2% (IC50: 10%) of the soluble plasma test composition solution. The suggestion is that the soluble plasma test composition is an antagonist (see FIG. 21).

Example 19

Inhibition of TACE

TNF-α is initially expressed on the cell surface as a 26-kDa, type II trans-membrane pro-form. The membrane-bound pro-TNF-α can then be cleaved between Ala-76 and Val-77 by a Zn-metalloprotease, TNF-α converting enzyme (TACE), resulting in the formation of the 17-kDa, mature, soluble cytokine.

TACE belongs to the family of metalloprotease disintegrins (also known as ADAM or MDC family), which are modular transmembrane proteins with a Zinc-dependent catalytic domain. Metalloprotease disintegrins are synthesized as inactive precursors containing a prodomain that blocks the activity of the catalytic domain. TACE is the predominant protease responsible for the generation of soluble TNF-α.

T cells derived from TACE$^{\Delta Zn/\Delta Zn}$ knockout mice have a 90% reduction in their ability to process pro-TNF-α. Levels of TACE protein and its enzymatic activity in the synovial tissue of patients with RA are significantly higher than those of patients with osteoarthritis. Therefore, TACE inhibitors, which inhibit the processing of pro-TNF-α on the plasma membrane, represent an appealing alternative to the neutralization of TNF-α by biological agents.

TACE is also required for the activation of the receptor for the epidermal growth factor (EGFR) in vivo and for the development of tumors in nude mice, indicating a crucial role of TACE in tumorigenesis. In agreement with this view, TACE is dramatically over-expressed in the majority of mammary tumors analyzed. Collectively, this evidence points to TACE as a promising target of anti-tumor therapy.

A large number of potent and differentially selective compounds have been designed, synthesised and patented as TACE inhibitors for the putative therapy of inflammatory disorders. A relatively large number of compounds can decrease the levels of TNF-α in cell and animal assays and display good efficacy, potency and bioavailability in cell and animal models of inflammatory disease. Several high efficacy compounds, such as BMS-561392 (in phase II for rheumatoid arthritis), have been taken to phase I and phase II clinical trials but no TACE inhibitor has yet made it to market. Another approach is a dual inhibitory effect of inhibition of TACE and selected MPP's, like that of Ro 32-7315.

The soluble plasma test composition of the present invention has been shown to reduce the release of TNF-α secretion by monocytes upon an LPS challenge as described in Examples 14 & 16. The suggestion is that the soluble plasma test composition also inhibits TACE.

Figure 22:
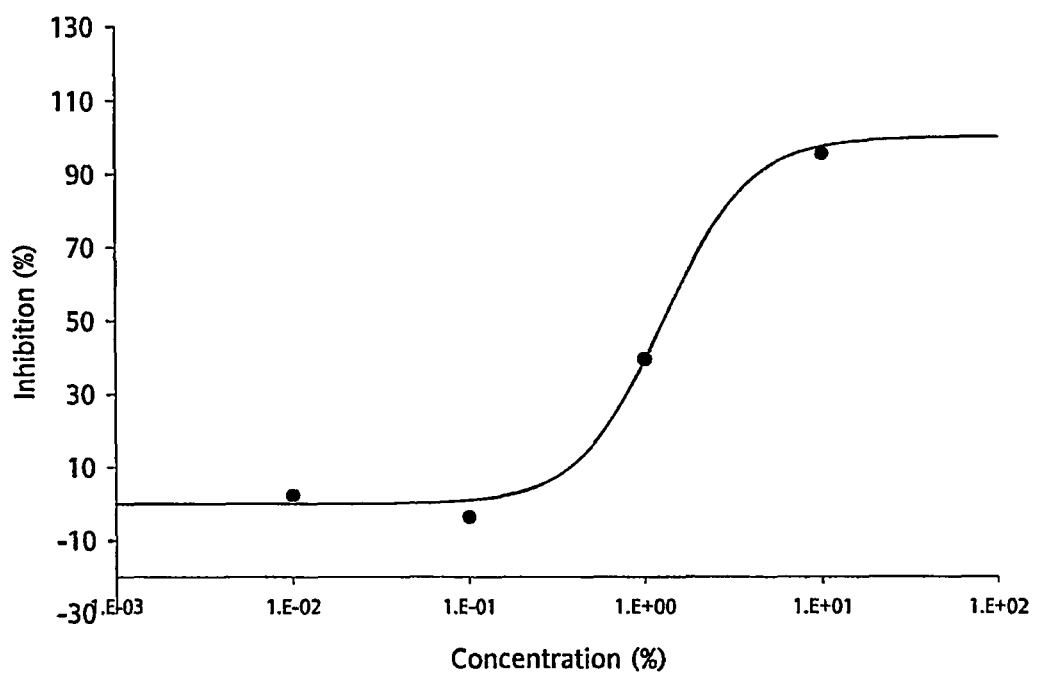
FIG. 22 shows a direct measurement of human TACE activity in human recombinant insect Sf21 under the influence of the composition of the present invention comprising zinc chloride, glycine and trypsinised protein. Test composition inhibited the TACE activity with an IC$_{50}$ of 1.3% of the test solution. TACE inhibition demonstrates an additional pathway through which the test compositions can reduce an inflammatory response.

A direct measurement of human TACE activity in human recombinant insect Sf21 cells revealed that the soluble plasma test composition of the present invention inhibited the TACE activity with an $IC_{50}$ of 1.3% of the soluble plasma test composition solution (see FIG. 22).

The active site of TACE is structurally similar to the 24 currently known metalloproteases. The activity of soluble plasma test composition against the metalloproteases will be tested to establish its selectivity and thereby its spectrum. First data demonstrate that MMP-3 is inhibited 72% by 10% of the soluble plasma test composition solution.

Example 20

Caspase Inhibition

The interleukin-1b converting enzyme ICE, now renamed caspase-1, is a cysteine endoprotease. The enzyme directly cleaves pro-IL-1 to mature cytokine IL-1b that is released into the extracellular environment. To date more than ten caspases are known. Much evidence has been accumulated to suggest that inhibition of caspase-1 can directly lead to a lowering of IL-1b in vitro and in vivo. This effect has been correlated with efficacy in ameliorating the symptoms of inflammation in many models of inflammatory diseases in animals and humans. Clinical trials data on pralnacasan and VX-765 have shown that caspase-1 inhibitors in general, can be effective for the treatment rheumatoid arthritis, osteoarthritis and psoriasis. Other pharmacological studies have also indicated that these inhibitors could be beneficial as therapeutic agents for a number of other disease states such as ischaemia/reperfusion injury and stroke. Of the few inhibitors that have entered clinical trials, all are reversible covalent (eg. aldehydes, pralnacasan and VX765) or irreversible inhibitors (eg. acyloxymethyl ketone 45). One possible problem with these compounds is their inherent reactive nature, which is not generally considered to be a desirable drug-like quality.

Caspases play a crucial role in mediating apoptosis. Thirteen members of the human caspase family have been identified. Some are involved in apoptosis, and these can be divided into two subgroups. The first group consists of caspase 8, caspase 9, and caspase 10, which function as initiators of the cell death process. The second group contains caspase 3, caspase 6, and caspase 7, which work as effectors, cleaving various substrates that ultimately cause the morphological and biochemical changes seen in apoptotic cells.

Apoptosis is a cellular response to a cellular insult such as UV light, chemical or physical damage or a viral infection. This insult initiates a cascade of events which lead to the destruction of the cell, often called "programmed cell death". It is an innate response of the cell which protects the rest of the organism. Exaggeration of apoptosis causes tissue-damage. Hepatitis, insulitis, graft-versus-host disease, and allergic encephalitis are due to the excessive apoptosis by the Fas ligand expressed on cytotoxic lymphocytes. Apoptotic cells are detected in the brain of ischemia or Alzheimer patients, suggesting that apoptosis is at least in part responsible for the disease manifestation. In stroke evidence has accumulated that neurons in the ischemic penumbra undergo apoptosis. In CD95 (APO-1/Fas)-deficient mice and in TNF-α-deficient mice, cerebral ischemic lesions were less. Mice injected with a mixture of neutralizing anti-TNF and anti-CD95L antibodies 30 min after induction of stroke have been reported to show a marked decrease in both infarct volumes and mortality. In the brain of Parkinson patients increased levels of inflammatory cytokines like caspase 1 and 3 have been reported.

Of all the known caspases, caspase-3 is believed to be the primary executioner of apoptosis. Activation of caspase-3, depending on the activating mechanism, can induce chromatin condensation, DNA fragmentation, and cleavage of the DNA repair enzyme poly (ADP-ribose) polymerase, and eventuate in programmed cell death. An inhibition of caspase-3 can directly block cell apoptosis in vitro. In animal models of Alzheimer's disease and traumatic brain injury, pharmacological caspase-3 inhibition reduced the extent of brain damage as well as suppressed the number of Aβ deposits.

Figure 23:
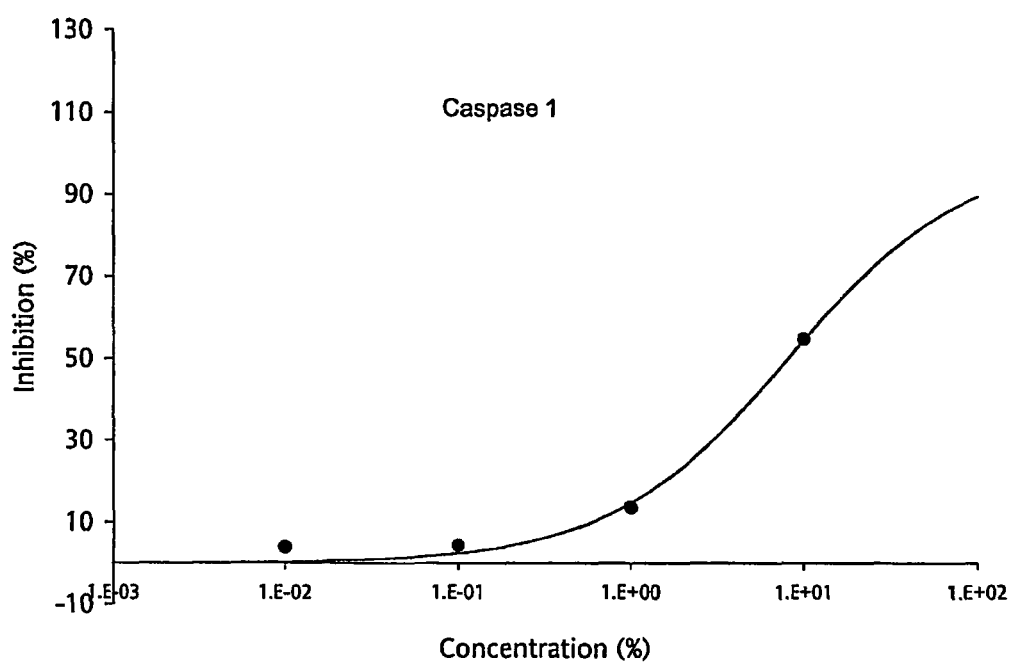
FIG. 23 shows the composition of the present invention comprising zinc chloride, glycine and trypsinised protein induced inhibition of human Caspase 1 in vitro with an IC$_{50}$ of 8.1% of the test sample solution.
Figure 24:
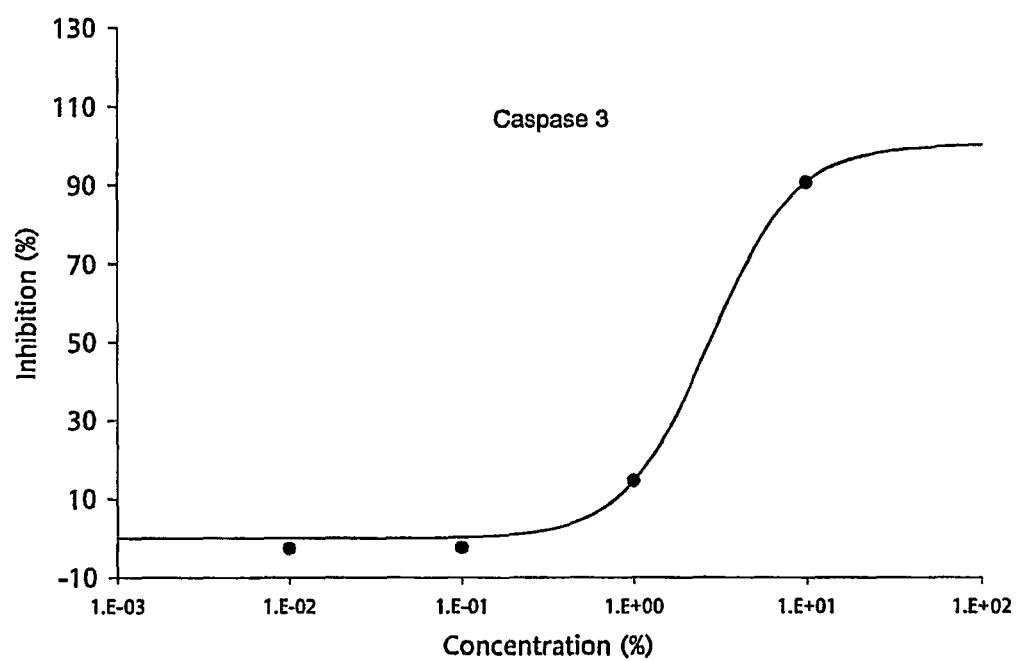
FIG. 24 shows the composition of the present invention comprising zinc chloride, glycine and trypsinised protein induced inhibition of human Caspase 3 in vitro. Test sample inhibited caspase 3 with an IC$_{50}$ of 2.8%.

The soluble plasma test composition of Example 14 was found to inhibit the human Caspase 1 with an $IC_{50}$ of 8.1% of the soluble plasma test composition solution. The Caspase 3 was inhibited with an $IC_{50}$ of 2.8% of the soluble plasma test composition solution. The Caspase 9 was inhibited 57% by 10% of the soluble plasma test composition solution (See FIGS. 23 & 24).

The inhibitory effects of the soluble plasma test composition on different Caspases motivates an extensive investigation of the various Caspases and the potential beneficial activity of soluble plasma test composition in apoptosis.

Example 21

Nitric Oxide Synthases: Inhibition and Stimulation

Nitric oxide (NO), first characterized as an endothelium-derived relaxation factor, has now emerged as a ubiquitous signalling messenger molecule involved in diverse pathophysiologic processes such as neurotransmission, inflammatory and immune responses, and vascular homeostasis. NO is synthesized from the amino acid L-arginine by a family of enzymes termed NO synthases (NOS).

There are three Nitric Oxide Synthases known sofar. There is a large number of small molecule inhibitors of the NOS with various selectivity. Apart from L-NAME which is being used in human subjects for research purposes only, to the knowledge of the company so far none has reached the clinical developmental stage. Naproxcinod is a novel, proprietary, nitric oxide-donating derivative of naproxen currently in a Phase III clinical study for osteoarthritis.

The iNOS releases NO in large quantities during inflammatory and host defence, immunological reactions, where it contributes to cytotoxicity against tumor cells, bacteria, viruses, and other invading microorganisms. The iNOSs bind calmodulin tightly and their activity is essentially Ca2+-independent. iNOS is activated by interleukin-17 (IL-17), which is a proinflammatory T cell cytokine. NO donors like sodium nitroprusside and S-nitroso-acetyl-DL-penicillamine were reported to inhibit carrageenan induced mouse paw oedema. NO can inhibit the production of the (TNF-α, IL-1, IL-6) of the immune and acute phase response caused by surgery and trauma.

The eNOS is expressed constitutively in endothelial cells and synthesizes the NO needed for regulation of blood pressure. The activation of eNOS is induced by increase in intracellular $Ca^{2+}$. The vascular tone of arteries is primarily steered by the availability of NO, leading to relaxation of the vessels. Likewise, the role of NO in neuronal degeneration of glaucoma is well established. Topical application of non-selective NOS inhibitor, nitro-L-arginine methyl ester (L-NAME), was effective in an experimental model of glaucoma (ocular hypertension) in rabbits. Studies with nitroglycerine, which releases No have indicated that NO may be the causative molecule in migraine other vascular headaches.

The nNOS is found in a variety of neurons in both the central and peripheral nervous systems and is a constitutionally expressed enzyme, though it can also be induced in neurons by certain treatments. NO acts as a neuromediator with functions, including the formation of memory, coordination between neuronal activity and blood flow, and modulation of pain. In peripheral nervous system, NO is released by nerves, which mediate some forms of neurologic vasodilatation and regulate certain gastrointestinal, respiratory, and genitourinary functions. Selective inhibition of generation of NO may be a useful therapy as in case of brain ischemia and chronic degenerative diseases of the nervous system.

The soluble plasma test composition of Example 14 has been found to have differential activity on the different Nitric Oxide Synthases.

Mouse macrophage inducible Nitric Oxide Synthase (iNOS) was found to be stimulated 93% by 10% of the soluble plasma test composition solution. Bovine endothelial Nitric Oxide Synthase (eNOS) was found to be inhibited 44% by 10% of the soluble plasma test composition solution. Rat neuronal Nitric Oxide Synthase (nNOS) was found to be inhibited 80% by 10% of the soluble plasma test composition solution.

The inhibition of the nNOS may have some neural disease implication (e.g. Migraine, Alzheimer).

Example 22

COX-1 and COX-2 Inhibition

Cyclooxygenase is the key enzyme in the synthesis of prostaglandins from arachidonic acid. In 1991, several laboratories identified a product from a second gene with Cox activity and called it Cox-2. Cox-1 is widely distributed in the body's cells, from the stomach to the platelets of the blood. Continuously present in the body, they serve "housekeeping" functions that maintain various normal physiological conditions. Cox-2 is induced by inflammatory and other injurious stimuli, and they tend to localize in the sites of injury, for instance the swelled joints of people suffering from rheumatoid arthritis. PGE2 has also been reported to enhance sensitization at the spinal cord resulting in hyperexcitability. Protective prostaglandins, which preserve the integrity of the stomach lining and maintain normal renal function in a compromised kidney, are synthesized by Cox-1. Gastrointestinal side effects of COX inhibitors are blamed for roughly 100,000 hospitalizations and 15,000 deaths each year in the United States alone. Therefore Cox-2 inhibitors, like Celebrex and Vioxx rapidly overhauled the non-selective Cox-inhibitory, like aspirin. However in late 2004, a major trial on long term treatment found that almost twice the subjects who took Vioxx for eighteen months had strokes or heart attacks than subjects on placebo. Vioxx was immediately withdrawn from the market. The strategy of using selective Cox-2 inhibitors is being reassessed. Most likely patients will benefit most when the treatment regime of non-selective Cox or Cox-2 inhibitors is taking into consideration possible Cox-inhibition sensitivities, treatment duration and route of application.

Figure 25:
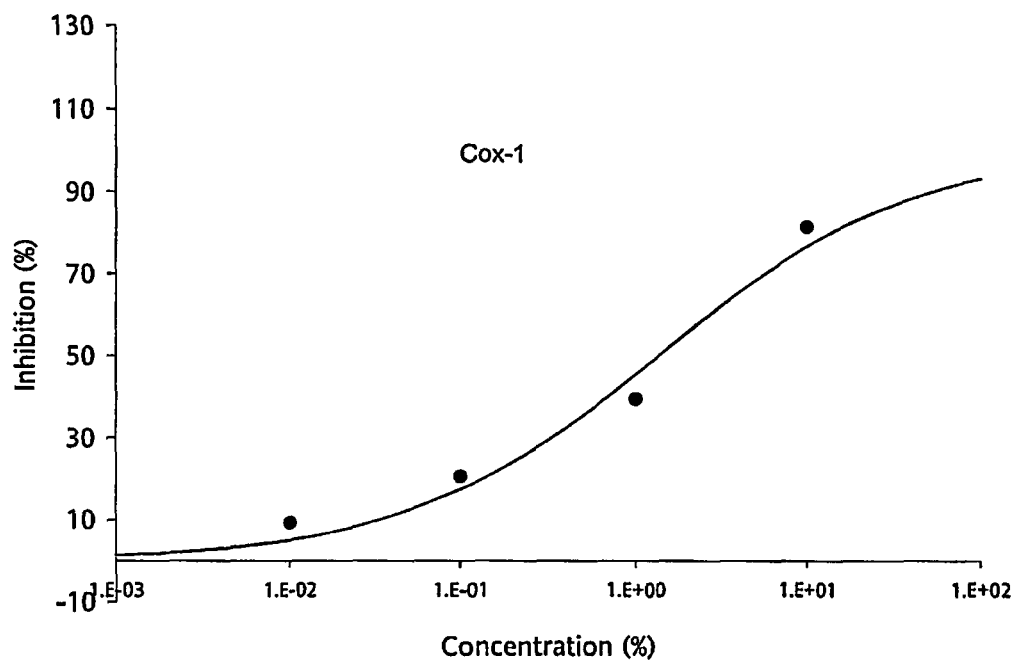
FIG. 25 shows inhibition of human platelet derived COX1 in vitro with the composition of the present invention comprising zinc chloride, glycine and trypsinised protein. COX1 inhibition is a known mechanism through which clinical inflammatory pain is reduced.
Figure 26:
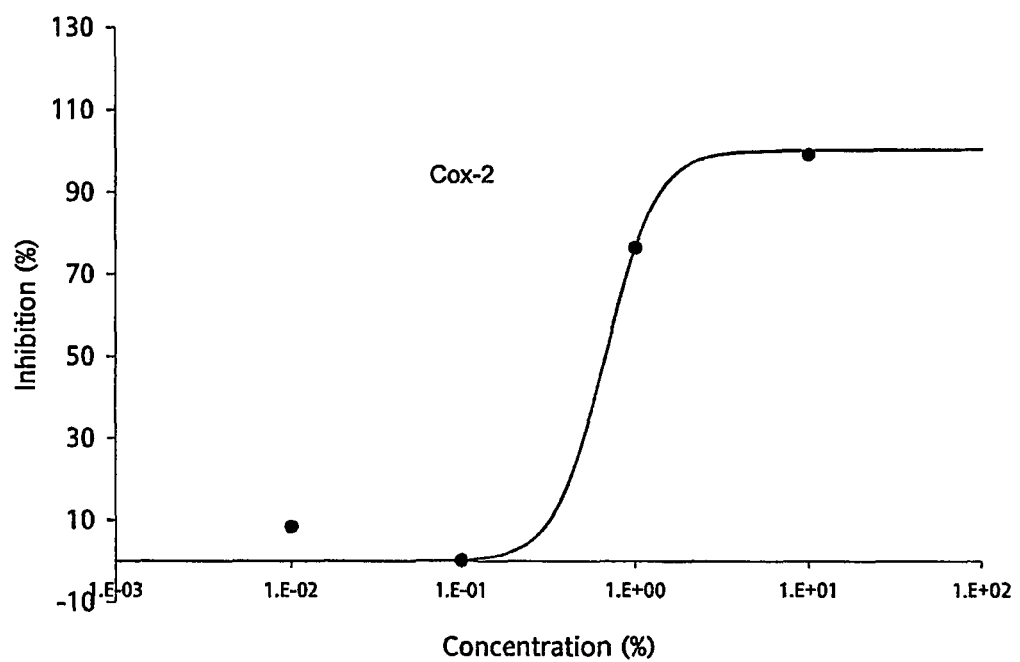
FIG. 26 shows inhibition of COX2 in human recombinant insect sf21 cells in vitro with the composition of the present invention comprising zinc chloride, glycine and trypsinised protein (IC$_{50}$ of 0.68% of the test composition). COX2 inhibition is a known mechanism through which clinical inflammatory pain is reduced.

As shown in FIGS. 25 and 26, the soluble plasma test composition was found to inhibit the human platelet Cyclooxygenase-1 (Cox-1) with an $IC_{50}$ of 1.4% of the soluble plasma test composition solution. The Cyclooxygenase-2 (Cox-2) was inhibited with an $IC_{50}$ of 0.686% of the soluble plasma test composition solution.

Example 23

Bradykinin Antagonism

Kinins are pro-inflammatory peptides that mediate numerous vascular and pain responses to tissue injury. Two pharmacologically distinct kinin receptor subtypes have been identified, which are named B1 and B2 and belong to the rhodopsin family of G protein-coupled receptors. The B2 receptor mediates the action of bradykinin (BK) and lysyl-bradykinin (Lys-BK), the first set of bioactive kinins formed in response to injury from kininogen precursors through the actions of plasma and tissue kallikreins, whereas the B1 receptor mediates the action of des-Arg9-BK and Lys-des-Arg9-BK, the second set of bioactive kinins formed through the actions of carboxypeptidases on BK and Lys-BK, respectively. The B2 receptor is ubiquitous and constitutively expressed, whereas the B1 receptor is expressed at a very low level in healthy tissues but induced following injury by various pro-inflammatory cytokines such as interleukin-1β. Both receptors act through Gαq to stimulate phospholipase Cβ followed by phosphoinositide hydrolysis and intracellular free $Ca^{2+}$ mobilization and through Gαi to inhibit adenylate cyclase and stimulate the mitogen-activated protein kinase pathways. The use of mice lacking each receptor gene and various specific peptidic and non-peptidic antagonists have implicated both B1 and B2 receptors as potential therapeutic targets in several pathophysiological events related to inflammation such as pain, sepsis, allergic asthma, rhinitis, and oedema, as well as diabetes and cancer.

Several B1 and B2 receptor antagonists, are and have been investigated pre-clinically and only few in clinical studies in a limited number of indications.

A polymorphism in the human B2 receptor gene is found in patients with hereditary angioedema. Accordingly Icatibant has shown positive clinical effects.

Increased production in kinins have been reported after concussive brain injury and spinal cord injury in rat and blunt trauma in humans. In animals, an involvement of the B2 receptor in the development of neurological deficit and the inflammation-induced secondary damage resulting from diffuse traumatic brain injury has been shown. The peptide B2 antagonists Deltibant has been reported to have a positive effect on the Glasgow Outcome Score in head trauma patients. In animal models of head injury, the non-peptide compound Anatibant reduced brain edema, improved long-term neurological function recovery and blunted the acute inflammatory response. Initial promising results have been reported and further clinical studies are underway. Initial data have been reported to indicate potential use for B1 receptor antagonists as antiepileptic agents, and for B2 receptor antagonists (and/or B1 agonists) in the treatment of stroke. Functional B1 receptors located on T-lymphocytes and on the blood brain-barrier may also suggest a use in multiple sclerosis.

In asthmatic subjects inhaled BK is a potent bronchoconstrictor, but has no such action in healthy subjects. Icatibant treatment led to a dose-dependent improvement in objective pulmonary function tests. The mechanism was interpreted as anti-inflammatory effect, while no acute bronchodilator effect was found. Persistent dry cough is a side effect related to the use of ACE inhibitors. The mechanism is not fully understood but can be attributed to a possible local accumulation of BK that may lead to activation of pro-inflammatory peptides and a local release of histamine, inducing a cough reflex hypersensitivity. Icatibant is expected to complete its phase 3 regulatory requirements in the latter part of 2006.

Further evidence of the clinical relevance of an interference in the Bradykinin function, may be derived from the Angiotensin Converting Enzyme (ACE) inhibitors, a major product class for treating hypertension. Classically ACE converts Ang I to its active form Ang II which has a strong vasopressor activity. Interestingly ACE has an about 100 fold higher affinity for Bradykinin. ACE inactivates Bradykinin by hydrolysis. Thus inhibition of ACE by e.g. Captopril, most likely also causes an increase in Bradykinin, which in turn has a vasodilatory effect. In cell models, ACE inhibition has been reported to stimulate the NO and prostacyclin (PGI2) production triggered by BK. In vivo, Icatibant has been shown to suppress the antihypertensive, anti-hypertrophic, and anti-proliferative effects of ACE inhibitors. In mice, ACE by degrading bradykinin significantly has been shown to control cutaneous inflammatory responses to allergens but not to irritants, which may explain the observed exacerbation of inflammatory skin disease in patients under medication with ACE inhibitors.

Figure 27:
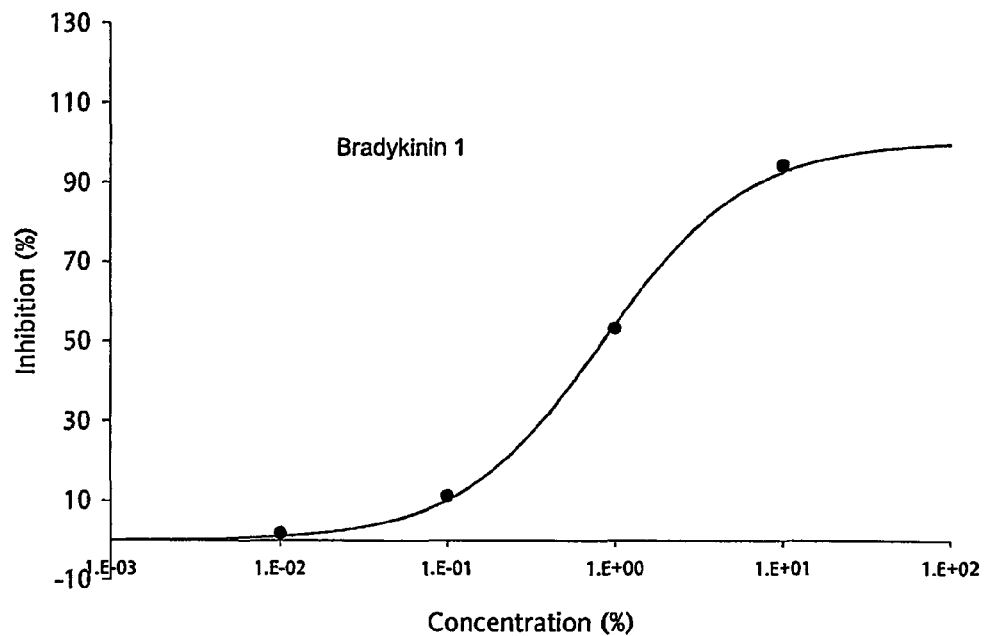
FIG. 27 shows competitive binding of the composition of the present invention comprising zinc chloride, glycine and trypsinised protein to the human Bradykinin 1 receptor compared with binding of [$^3$H]-(Des-Arg$^{10}$)-Kallidin in human IMR-90 cells. Test composition was found to bind to the human Bradykinin 1 receptor with a K$_i$ of 0.22% (IC$_{50}$: 0.85%) of the test solution. Bradykinin 1 receptor is heavily involved in inflammatory pain.
Figure 28:
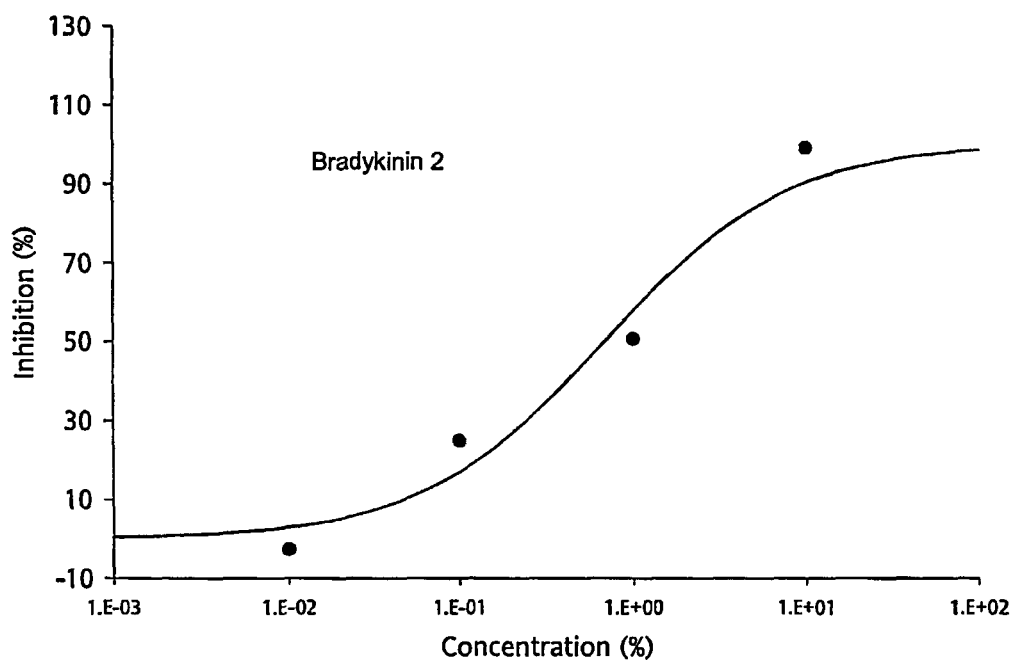
FIG. 28 shows competitive binding of the composition of the present invention comprising zinc chloride, glycine and trypsinised protein to the human Bradykinin 2 receptor compared with binding of [$^3$H]-Bradykinin in human recombinant CHO-K1 cells. Binding to the human Bradykinin 2 receptor was a K$_i$ of 0.41% (IC$_{50}$=0.69%) of the soluble plasma precipitate composition of the present invention. The bradykinin 2 receptor is an important mechanism during pain and inflammation.

Binding to the human Bradykinin 1 receptor was analysed by competition with binding of [$^3$H]-(Des-Arg10)-Kallidin and for the Bradykinin 2 receptor [$^3$H]-Bradykinin. The soluble plasma test composition of Example 14 was found to bind to the human Bradykinin 1 receptor with a Ki of 0.22% ($IC_{50}$: 0.85%) of the soluble plasma test composition solution. Binding to the human Bradykinin 2 receptor was a Ki of 0.41% ($IC_{50}$=0.69%) of the soluble plasma test composition solution of Example 14 (see FIGS. 27 to 28).

Example 24

Cannabinoid Receptors

Two receptor subtypes have been cloned to date. CB1 activation decreases neurotransmitter release in pain pathways, thus reducing pain transmission. CB1 activation results in augmented membrane hyperpolarisation and inhibition of neurotransmitter release. The CB1 receptors are highly expressed throughout the peripheral and central nervous systems, and especially at nervous system sites important for nociceptive processing. There is abundance of preclinical evidence that CB1 agonists work in acute pain, acute inflammation, chronic pain (eg neuropathic), and chronic inflammatory pain. Efficacy of currently available CB1 agonists in humans is modest, mainly due to an unfavourable therapeutic index.

CB2 is highly expressed in immune system related tissues, such as spleen, tonsils, and immune cells. Under inflammatory conditions, its expression is increased in the affected tissues. Pharmacologically CB2 agonists are effective in reducing inflammatory pain, while there is no evidence of specific analgesic activity. They act via modulation of cytokines and chemokines. CB2 expression is generally increased under chronic disease states with an inflammatory component. CB2 agonists can down-regulate the immune response. Non-selective canabinoids are clinically used in the inhalable form for reducing discomfort in chronic pain states, especially in cancer pain. However, it is not clear which subtype of the cannabinoid receptor is responsible for the therapeutic effect. Most likely combined CB1 and CB2 agonism is the best therapeutic mechanism.

A combination of CB1 and CB2 agonistic activity is being discussed as having the most optimal efficacy. The stumbling block in the development of these drugs is their blood-brain-barrier penetration and related side-effects.

By preventing BBB penetration, it is expected that the psychoactive side-effects are non-existent. In the case of the soluble plasma test composition, the topical application might be suitable for local pain control, while not becoming systemically available.

The activation of the cannabinoid system has also demonstrated preclinical efficacy in neuroprotection in degenerative disorders of the nervous system, such as multiple sclerosis, Parkinson's disease, and Alzheimer's disease. For instance, through activation of the MAPK pathway, CB1 agonists could protect neurons from the toxicity of the amyloid β protein in vitro. In vivo, the neurotoxic effects of 6-hydroxydopamine, a toxin used to induce Parkinson-like states in rats, was reduced with cannabinoid agents. Cannabinoids have also been experimentally shown to reduce the CNS inflammatory and neurodegenerative response associated with multiple sclerosis. Cannabinoids (CB1 or CB2 receptors) inhibit LPS-mediated induction of iNOS in microglia, inhibit activation of microglia by β amyloid in vitro and in vivo and prevent the cognitive dysfunction and neuronal death induced by intracerebral β amyloid administration in rats. In addition, cannabinoids directly protect neurons from glutamate-mediated excitotoxicity, in vitro and in vivo and act on excitatory pre-synaptic terminals to suppress glutamate release. Microglia can express CB2 receptors and neurons only CB1 receptors. Therapeutic agents thus most likely shall be CB1/CB2 antagonists. However, discussions are ongoing as to the precise nature of these neuroprotective effects.

Figure 30:
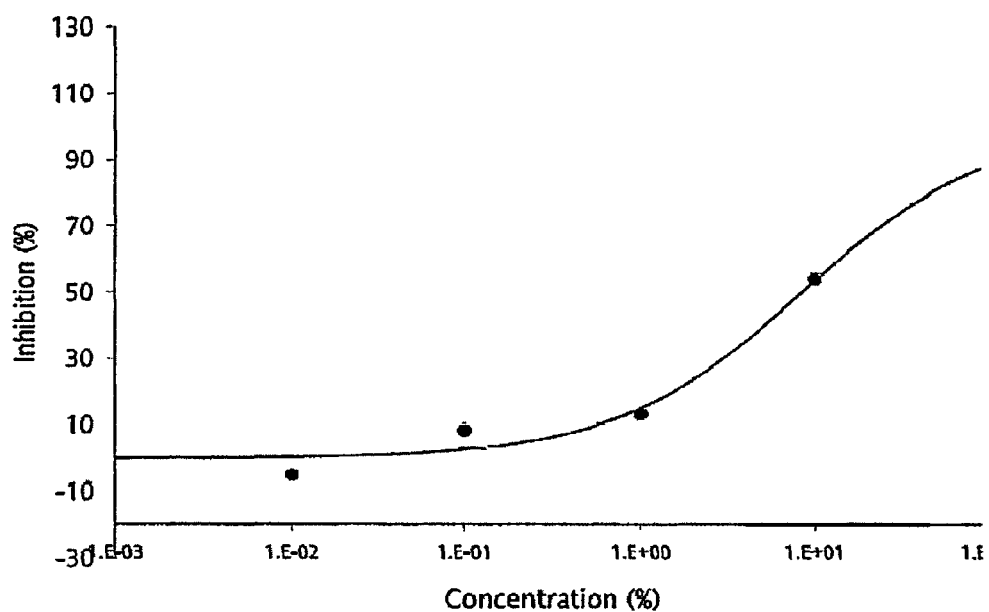
FIG. 30 shows competitive binding to the cannabinoid receptor1 in human recombinant HEK-293 cells. The composition of the present invention comprising zinc chloride, glycine and trypsinised protein binds with a K$_i$ of 6.1% (IC$_{50}$ 8.5%) of the test sample solution. Cannabinoid receptors are mechanisms strongly involved in pain sensation.

The soluble plasma test composition of Example 14 binds to the human CB1 receptor with a Ki of 6.1% ($IC_{50}$ 8.5%) of the soluble plasma test composition solution. Binding to the CB2 receptor was less, giving only 33% displacement by 10% of the soluble plasma test composition solution (see FIG. 30).

Example 25

CCR Receptors

The allergic airway inflammation of asthma is characterized by the recruitment of eosinophils from the blood into the airways. Eosinophils are able to contribute to the inflammatory response by release of mediators that induce bronchoconstriction, increased microvascular permeability, and mucus formation, and through the release of toxic granule contents that cause tissue damage in the lungs. Eosinophils may further contribute to the inflammatory response through their abilities to function as APC.

CCR1 is closely related to CCR3, which is the main chemokine receptor to regulate eosinophil accumulation. CCR1 is expressed by basophils, monocytes, and memory T cells.

15-20% of people have high levels of CCR1 expressed by eosinophils. Eosinophils from these donors are highly responsive to CCL3/macrophage-inflammatory protein MIP-1α. CCL3 expression is increased in human asthmatic lung. These findings suggest that CCR1 or CCR3 block or antagonism can be therapeutic in asthmatic conditions.

Also in severe respiratory virus infections, the associated inflammation through the MIP-1alpha/CCR1 pathway should be addressed with an antagonistic therapy. A CCR1 antagonist should in this case be used in conjunction with anti-viral strategies. For instance, in mice an infection with the natural rodent pathogen pneumonia virus was limited by the antiviral agent ribavirin. However, the antiviral therapy had no impact on morbidity and mortality when the antiviral agent was not accompanied by the immunomodulator Met-RANTES to counteract the MIP-1 mediated inflammation.

RA patients treated with a potent and selective antagonist of CCR1 were reported to show a clear reduction in synovial inflammation.

Figure 29:
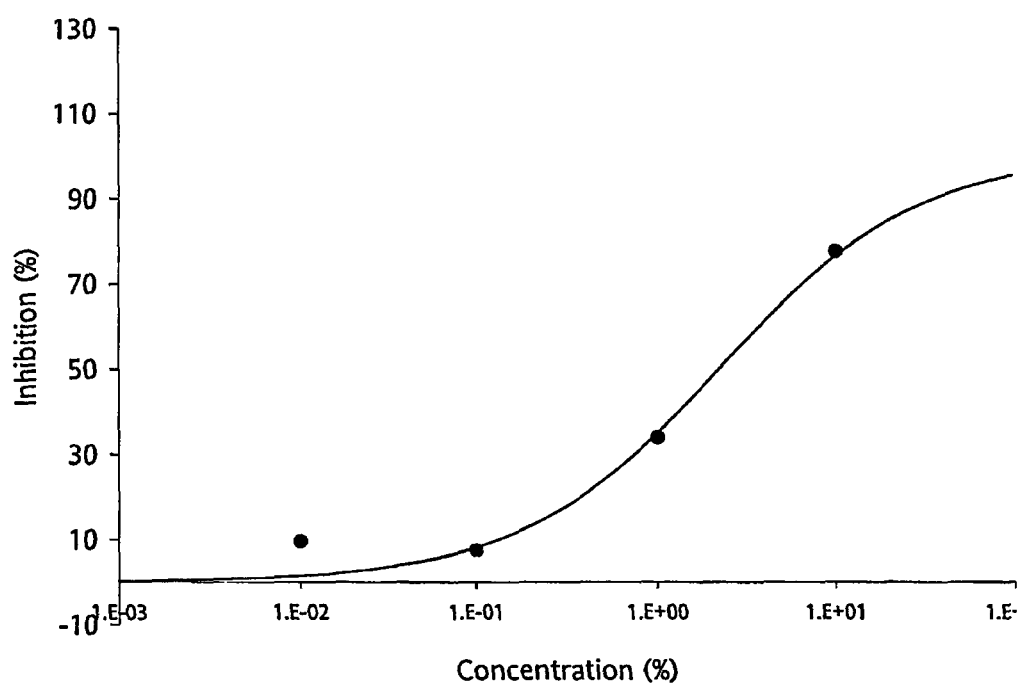
FIG. 29 shows competitive binding of the composition of the present invention comprising zinc chloride, glycine and trypsinised protein to the human CCR1 receptor, assessed by competition with [$^{125}$I] MIP-1α. The K$_i$ value was 1.0% (IC$_{50}$ 2.2%) of the Test sample. CCR1 receptors are heavily involved in inflammatory processes, such as airway inflammation.

The soluble plasma test composition of Example 14 binds to the human CCR1 receptor, assessed by competition with [$^{125}$I] MIP-1α with a Ki of 1.0% (IC$_{50}$ 2.2%) of the soluble plasma test composition solution (see FIG. 29).

Example 26

Other Effects Analyzed

The soluble plasma test composition inhibited the binding of [$^3$H] Prostaglandin E2 (PGE2) to its receptor on human recombinant HEK-293 cells with a Ki of 0.89% (IC$_{50}$=2.0%) of the soluble plasma test composition solution. This most likely supports the anti-inflammatory and anti-pain activity of the soluble plasma test composition.

The soluble plasma test composition has a minimal (39% inhibition) ligand-binding to the vanilloid receptor ([$^3$H] resiniferatoxin binding to Wistar Rat spinal cord) at 10% of the soluble plasma test composition solution.

10% of the soluble plasma test composition solution inhibited the binding of [$^3$H] Quisqulic acid (mGlu5 glutamate receptor) to human recombinant CHO—K1 cells by 63% and the binding of [$^3$H] MDL-105519 (NMDA receptor) to Wistar rat cerebral cortex by 109%. Especially the binding to the NMDA receptor deserves further attention.

10% of the soluble plasma test composition solution inhibited the human recombinant Protein Kinase C (PKCγ) 100%.

Interestingly, the soluble plasma test composition of the present invention has some affinity to the opiate receptors, resulting in 41% displacement of the ligand binding to the δ-, 38% to the κ-opiate receptor subtypes in human recombinant cells at 10% of the soluble plasma test composition solution.

SUMMARY

Table 15 shows the targets and the effects shown by the soluble plasma test composition of the present invention.

TABLE 15

| Target | Effect | Effect of 10% test composition | K$_i$ | IC$_{50}$ |
|---|---|---|---|---|
| TNF-α receptor | Binding | 50% | 7.2% | 10% |
| TACE inhibition | Inhibition | 100% | | 2.5% |
| TACE | Inhibition | 95% | | 1.3% |
| MPP-3 | Inhibition | 72% | | |
| MPP-9 | Inhibition | 5% | | |
| Caspase-1 | Inhibition | 55% | | 8.1% |
| Caspase-3 | Inhibition | 90% | | 2.8% |
| Caspase-9 | Inhibition | 57% | | |
| iNOS | Stimulation | 93% | | |
| eNOS | Inhibition | 44% | | |
| nNOS | Inhibition | 80% | | |
| Cox-1 | Inhibition | 81% | | 1.4% |
| Cox-2 | Inhibition | 92% | | 0.7% |
| PKC$_γ$ | Inhibition | 100% | | |
| Bradykinin 1 receptor | Binding | 94% | 0.2% | 0.8% |
| Bradykinin 2 receptor | Binding | 99% | 0.4% | 0.7% |
| CB1 receptor | Binding | 54% | 6.1% | 8.5% |
| CB2 receptor | Binding | 33% | | |
| LPS-induced IL-6 secretion | Inhibition | 33% | | |
| LPS-induced IL-1β secret. | Inhibition | 41% | | |
| PGE$_2$ receptor | Binding | 84% | 0.9% | 2.0% |
| Chemokine CCR1 receptor | Binding | 73% | 2.2% | 1.0% |
| Vanilloid receptor | Binding | 39% | | |
| Glutamate mGlu$_5$ receptor | Binding | 63% | | |
| Glutamate NMDA | Binding | 109% | | |
| δ-opiate receptor | Binding | 41% | | |
| κ-opiate receptor | Binding | 38% | | |

Table 16 shows the biochemical mechanisms that are associated with the different diseases and conditions.

TABLE 16

| Indication | Mechanism |
|---|---|
| Arthritis | TNF-α antagonism |
| | TACE inhibition |
| | Caspase inhibition |
| | COX inhibition |
| | Bradykinin antagonism |
| | PGE$_2$ receptor antagonism |
| Muscular pain | Bradykinin antagonism |
| | PGE$_2$ antagonism |
| | Opiate receptor agonism |
| | COX inhibition |
| | TNF-α antagonism |
| | TACE inhibition |
| Psoriasis | TNF-α antagonistm |
| | Caspase inhibition |
| Asthma | Bradykinin antagonism |
| | CCR1 antagonism |
| COPD | Bradykinin antagonism |
| | TNF inhibition |
| | TACE inhibition |
| | CCR1 antagonism |
| Cancer | TACE inhibition |
| | iNOS stimulation |
| | Bradykinin antagonism |

TABLE 16-continued

| Indication | Mechanism | |
|---|---|---|
| Cosmetic surgery | | TNF-α antagonism |
| | Dermabrasion | TACE inhibition |
| | Resurfacing | iNOS stimulation |
| | Liposuction | Caspase inhibition |
| | Contact dermatitis | Bradykinin antagonism |
| | | TNF-α antagonism |
| | | TACE inhibition |
| | | PGE2 antagonism |
| | | CB agonism |
| | | Opiate receptor agonism |
| | Asteatotic eczema | TNF-α antagonism |
| | | TACE inhibition |
| | Actinic skin keratosis | COX inhibition |
| | | PGE2 antagonism |
| | Inflammatory pain | TNF-α antagonism |
| | | TACE inhibition |
| | | COX inhibition |
| | | Bradykinin antagonism |
| | | PGE2 antagonism |
| | Brain ischemia | Caspase inhibition |
| | | eNOS inhibition |
| | | Bradykinin antagonism |
| | | CB1 agonism |
| | | TACE inhibition |
| | CNS degenerative diseases | Caspase inhibition |
| | | eNOS inhibition Caspase inhibition |
| | | TNF-α antagonistm |
| | | TACE inhibition |
| | | CB agonism |
| | Brain injury (traumatic) | Bradykinin antagonism |
| | | CB1 |
| | | TACE inhibition |
| | | TNF-α antagonism |
| | | Caspase inhibition |
| | Ankylosing spondylitis | TNF-α antagonism |
| | | TACE inhibition |
| | Lupus Crohn's disease | COX inhibition |
| | Post-operative pain | TNF-α antagonist |
| | | TACE inhibition |
| | | Bradykinin antagonism |
| | | CB1 agonists |
| | | PGE$_2$ antagonism |
| | | COX inhibition |
| | | Opioid agonism |
| | Neuropathic pain | CB1 agonism |
| | | Opiate agonism |
| | Tension headache | Bradykinin antagonism |
| | Temporo mandibular pain | Opiate agonism |
| | | CB1 agonism |
| | | PKCγ |
| | | NMDA antagonism |
| | | mGluR5 |
| Trauma (sports related) | | TNF-α antagonism |
| | | TACE inhibition |
| | | Caspase inhibition |
| | | CB1 agonism |
| | | Opiate agonism |
| Repetitive strain injury (sports related) | | TNF-α antagonism |
| | | TACE inhibition |
| | | Caspase inhibition |
| | | COX inhibition |
| | | Bradykinin receptor antagonism |
| | | PGE2 antagonism |
| Sunburn | | TNF-α antagonism |
| | | TACE inhibition |
| | | Caspase inhibition |

It should be noted that in all experiments supra the viability of cells, both test and control, were assessed visually. In all instances the cells exposed to soluble plasma test composition were viable as indicated by typical cell spreading over the culture vessel. The cell spreading noted was the same as the cell spreading noted from the non-challenged/non-treated cells.

The invention claimed is:

1. A method of increasing or decreasing cytokine levels or activity in an isolated human cell, said method comprising contacting the cell with an effective amount of a composition said composition comprising a mixture of denatured plasma protein and at least one metal ion or metal salt, wherein said composition is produced by:
   (a) mixing isolated plasma with sodium bicarbonate (NaHCO$_3$) and incubating said mixture for sufficient time and at a temperature of no more than 80° C. to produce a precipitate of denatured plasma proteins; and
   (b) isolating and resolubilising said precipitate in the presence of an aqueous solution at a temperature of between about 80° C. and about 150° C., wherein either before, during or after the resolubilising step at least one metal ion or metal salt thereof is admixed and wherein said cytokines are selected from the group consisting of tumour necrosis factor alpha (TNF-α), interleukin 1 beta (IL-1β), interleukin 6 (IL-6), tumour necrosis factor alpha converting enzyme (TACE), macrophage-inflammatory protein 1 alpha (MIP-1α), cyclooxygenase-1 (Cox-1) and cyclooxygenase-2 (Cox-2).

2. The method of claim 1, wherein the plasma is isolated from an animal selected from the group consisting of a human, an equine, a bovine, an ovine, a murine, a caprine and a canine.

3. The method of claim 1, wherein the plasma protein is further treated with a protease selected from the group consisting of trypsin, chymotrypsin, factor Xa, venom-protease, thrombin, plasmin and a serine-protease of the subtilisin family.

4. The method of claim 3, wherein the protease is trypsin.

5. The method of claim 1, wherein the metal ion is selected from the group consisting of nickel, sodium, copper, zinc, cobalt, iron, magnesium, manganese, potassium, silver and mercury, ions or salts thereof and mixtures thereof.

6. The method of claim 1, wherein the metal ion is a mixture of metals consisting essentially of nickel sulfate heptahydrate (NiSO$_4$.7H$_2$O), sodium fluoride (NaF), copper (III) sulfate penthydrate (CuSO$_4$.5H$_2$O), zinc chloride (ZnCl$_2$), hexaammonium heptamolybdate tetrahydrate ((NH$_4$)$_6$Mo$_7$O$_{24}$.4H$_2$O), cobalt (II) chloride hexahydrate (CoCl$_2$.6H$_2$O), iron (II) sulfate heptahyrate (FeSO$_4$.7H$_2$O), magnesium sulfate heptahydrate (MgSO$_4$.7H$_2$O, boric acid (H$_3$BO$_3$), manganese dichloride tetrahydrate (MnCl$_2$.4H$_2$O) and potassium chromate (K$_2$CrO$_4$).

7. The method of claim 1, wherein the increasing of cytokine levels is an increase in IL-6 and IL-1β secretion levels.

8. The method of claim 1, wherein the increasing of cytokine activity is an increase in activity of TNF-α, TACE, MIP-1α, Cox-1 or Cox-2.

* * * * *